United States Patent [19]

Nimmesgern et al.

[11] Patent Number: 4,956,366
[45] Date of Patent: Sep. 11, 1990

[54] SUBSTITUTED THIENOIMIDAZOLE DERIVATIVES, A PROCESS FOR THE PREPARATION THEREOF, PHARMACEUTICAL COMPOSITIONS CONTAINING THEM, AND THE USE THEREOF AS INHIBITORS OF GASTRIC ACID SECRETION, AS GASTROPROTECTIVES AND AS MEDICAMENTS FOR INTESTINAL INFLAMMATIONS

[75] Inventors: Hildegard Nimmesgern, Frankfurt am Main; Klaus Weidmann, Kronberg/Taunus; Hans-Jochen Lang; Robert Rippel, both of Hofheim am Taunus; Andreas W. Herling, Bad Camberg, all of Fed. Rep. of Germany

[73] Assignee: Hoechst Aktiengesellschaft, Frankfurt am Main, Fed. Rep. of Germany

[21] Appl. No.: 218,386

[22] Filed: Jul. 13, 1988

[30] Foreign Application Priority Data

Jul. 15, 1987 [DE] Fed. Rep. of Germany ....... 3723327

[51] Int. Cl.⁵ .................. C07D 403/12; A61K 31/415
[52] U.S. Cl. .................... 514/235.8; 544/122; 544/123; 544/295; 544/296; 544/298; 544/310; 544/316; 544/317; 544/318; 544/319; 544/327; 548/323
[58] Field of Search ................ 548/323; 544/295, 296, 544/317, 318, 319, 310, 237, 284, 235, 122, 123, 298; 514/235.8, 269, 274

[56] References Cited

U.S. PATENT DOCUMENTS

| | | | |
|---|---|---|---|
| 4,045,563 | 0/1977 | Berntsson et al. | 424/263 |
| 4,055,647 | 10/1977 | Arxa et al. | 514/274 |
| 4,472,409 | 0/1984 | Senn-Bilfinger | 424/263 |

FOREIGN PATENT DOCUMENTS

| | | |
|---|---|---|
| 0005129 | of 1979 | European Pat. Off. |
| 0178438 | of 1986 | European Pat. Off. |
| 0198583 | of 1986 | European Pat. Off. |
| 3639926 | 6/1988 | Fed. Rep. of Germany ...... 548/323 |

*Primary Examiner*—Mary C. Lee
*Assistant Examiner*—Catherine Scalzo

*Attorney, Agent, or Firm*—Finnegan, Henderson, Farabow, Garrett, and Dunner

[57] ABSTRACT

Substituted thienoimidazole derivatives, a process for the preparation thereof, pharmaceutical compositions containing them, and the use thereof as inhibitors of gastric acid secretion, as gastroprotectives and as medicaments for intestinal inflammations The invention relates to compounds of the formula

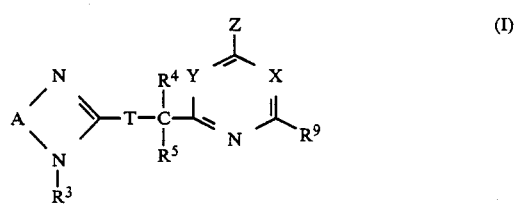

(I)

in which A represents

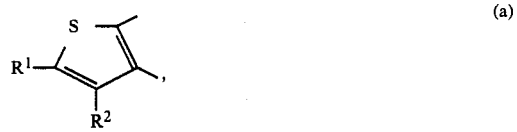

(a)

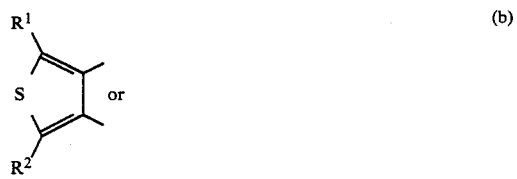

(b)

or

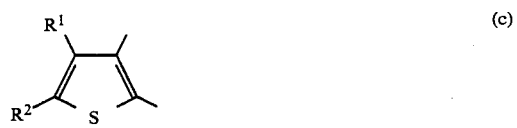

(c)

T denotes —S—, —SO— or —SO₂—, $R^1$ to $R^{10}$, X, Y and Z have the meanings indicated in the description, to a process for the preparation thereof, to pharmaceutical compositions containing them, and to the use thereof as inhibitors of gastric acid secretion, as gastroprotectives and as medicaments for intestinal inflammations.

8 Claims, No Drawings

SUBSTITUTED THIENOIMIDAZOLE DERIVATIVES, A PROCESS FOR THE PREPARATION THEREOF, PHARMACEUTICAL COMPOSITIONS CONTAINING THEM, AND THE USE THEREOF AS INHIBITORS OF GASTRIC ACID SECRETION, AS GASTROPROTECTIVES AND AS MEDICAMENTS FOR INTESTINAL INFLAMMATIONS

Benzimidazole derivatives acting to inhibit gastric acid secretion as disclosed in, for example, DE-A No. 2,548,340, EP-A Nos. 5129, 178,438, 198,583 and DE-A No. 3,240,248.

The present invention relates to thienoimidazole derivatives of the formula I

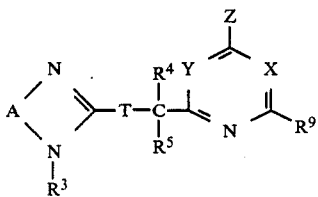

in which
A represents

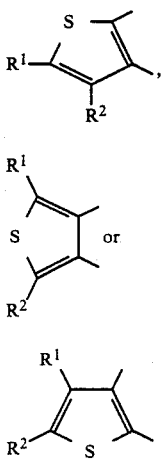

T denotes —S—, —SO— or —SO$_2$—, $R^1$ and $R^2$ are identical or different and denote hydrogen, halogen, cyano, nitro, trifluoromethyl, ($C_1$–$C_6$)-alkyl, ($C_1$–$C_6$)-hydroxyalkyl, ($C_1$–$C_6$)-alkoxy, ($C_1$–$C_4$)-fluoroalkoxy, —OCF$_2$Cl—, —O—CF$_2$—CHFCl, ($C_1$–$C_6$)alkylmercapto, ($C_1$–$C_6$)-alkylsulfinyl, ($C_1$–$C_6$)alkylsulfonyl, ($C_1$–$C_6$)-alkylcarbonyl, ($C_1$–$C_6$)alkoxycarbonyl, carbamoyl, N-($C_1$–$C_4$)-alkylcarbamoyl, N,N-di-($C_1$–$C_4$)-alkylcarbamoyl, ($C_1$–$C_6$)-alkylcarbonyloxy, ($C_3$–$C_8$)-cycloalkyl, phenyl, benzyl, phenoxy, benzyloxy, anilino, N-methylnilino, phenylmercapto, phenylsulfonyl, phenylsulfinyl, sulfamoyl, N-($C_1$–$C_4$)-alkylsulfamoyl or N,N-di-($C_1$–$C_4$)-alkylsulfamoyl, or, if A is defined as above under (a) or (c), can also together denote —[CH$_{2-n}$— or —CH=CH—CH=CH—, with one CH$_2$ group optionally being replaced by O, S, SO or SO$_2$, $R^3$ denotes hydrogen, alkanoyl, ($C_1$–$C_6$)-alkylcarbamoyl or another physiologically tolerated N$^{im}$ protective group which can preferably be eliminated in an acid medium and/or under physiological conditions, $R^4$ and $R^5$ are identical or different and denote hydrogen or ($C_1$–$C_3$)-alkyl, X denotes nitrogen, and Y denotes CR$^6$, or X denotes CR$^6$, and Y denotes nitrogen, $R^6$ denotes hydrogen, halogen, ($C_1$–$C_6$)-alkyl, trifluoromethyl, ($C_1$–$C_6$)-alkoxy, —O—C$_p$H$_{(2p+1-q)}$F$_q$, ($C_1$–$C_6$)alkoxy, ($C_1$–$C_6$)-alkyl, ($C_6$–$C_{12}$)-aryl, ($C_6$–$C_{12}$)-aryl($C_1$–$C_6$)-alkoxy, ($C_1$–$C_9$)-heteroaryl, ($C_6$–$C_{12}$)-aryloxy, it being possible for the corresponding aryl moiety to be optionally substituted by halogen or trifluoromethyl, or denotes cyano, nitro, ($C_1$–$C_6$)-alkylamino, di-($C_1$–$C_6$)-alkylamino, or amino, Z denotes NR$^7$R$^8$, OR$^{10}$ or SR$^{10}$, $R^7$ and $R^8$ are identical or different and denote hydrogen, ($C_1$–$C_6$)-alkyl, ($C_6$–$C_{12}$)-aryl, ($C_7$–$C_{13}$)aralkyl or ($C_3$–$C_6$)-cycloalkyl, or represent, together with the nitrogen to which they are bonded, azetidino, pyrrolidino, piperidino, piperazino, morpholino or N-($C_1$–$C_4$)-alkylpiperazino, each of which is optionally substituted by one or two identical or different ($C_1$–$C_6$)-alkyl groups, $R^9$ denotes hydrogen, halogen, ($C_1$–$C_3$)-alkyl, ($C_1$–$C_4$)alkoxy, benzyloxy or ($C_1$–$C_7$)-alkoxy-($C_1$–$C_3$)-alkyl, $R^{10}$ denotes hydrogen, ($C_1$–$C_4$)-alkyl, ($C_7$–$C_{13}$)-aralkyl, ($C_6$–$C_{12}$)-aryl, vinyl, allyl or a substituted alkyl radical of the formula C$_p$H$_{(2p+1-q)}$F$_q$, n is 3 or 4, p is 1, 2, 3 or 4, in particular 2 or 4, and q is 1 to (2 p+1), in particular 3 to 7, and to the physiologically tolerated salts thereof.

1H-Thieno[3,4-d]imidazole derivatives of the formula I in which A is as defined above under (b) are preferred. Further preferred compounds of the formula I are those in which $R^9$ represents hydrogen. T is preferably an —SO—group.

Particularly preferred compounds of the formula I are those in which

A is preferably as defined above under (b),

T preferably denotes an —SO— group, $R^1$ and $R^2$ are identical or different and denote hydrogen, ($C_1$–$C_3$)-alkyl, halogen, ($C_1$–$C_4$)-alkoxy or ($C_1$–$C_4$)alkoxycarbonyl, $R^3$ is as defined above, $R^4$ and $R^5$ each denote hydrogen, $R^6$ denotes amino, hydrogen, halogen, ($C_1$–$C_6$)-alkyl, ($C_1$–$C_6$)-alkoxy, —O—C$_p$H$_{(2p+1-q)}$F$_q$, ($C_6$–$C_{12}$)-aryloxy, ($C_6$–$C_{12}$)-aryl-($C_1$–$C_6$)-alkoxy, it being possible for the corresponding aryl moiety to be optionally substituted by halogen or trifluoromethyl, or denotes cyano, nitro, (C1-C6)-alkylamino, di-($C_1$–$C_6$)-alkylamino or ($C_1$–$C_6$)-alkoxy-($C_1$–$C_3$)-alkyl, with $R^6$ particularly being hydrogen, chlorine, ($C_1$–$C_6$)-alkyl, ($C_1$–$C_6$)alkoxy or C$_p$H$_{(2p+1-q)}$F$_q$, $R^7$ and $R^8$ represent, together with the nitrogen to which they are bonded, azetidino, piperazino, pyrrolidino, morpholino, piperidino or N-($C_1$–$C_4$)-alkylpiperazino, or both denote hydrogen, or $R^7$ is hydrogen and $R^8$ is a ($C_3$–$C_6$)-cycloalkyl group, but are preferably identical or different and represent hydrogen or ($C_1$–$C_6$)-alkyl or, together, represent piperidino, pyrrolidino, piperazino or morpholino and/or $R^9$ is hydrogen $R^{10}$ denotes hydrogen, ($C_1$–$C_4$)-alkyl, ($C_6$–$C_{12}$)-aryl, ($C_7$–$C_{13}$)-aralkyl, vinyl, allyl, C$_p$H$_{(2p+1-q)}$F$_q$, with alkyl preferably being methyl, ethyl, isopropyl, n-propyl, n-butyl, sec-butyl or tert-butyl, and aralkyl preferably being benzyl,
but in particular compounds of the formula I in which
A is preferably as defined above under (b),
T preferably denotes an —SO— group,
$R^1$ and $R^2$ are identical or different and denote hydrogen or $(C_1-C_3)$-alkyl,
$R^3$ denotes hydrogen,
$R^4$ and $R^5$ each denote hydrogen,
$R^6$ denotes hydrogen, $(C_1-C_6)$-alkoxy, trifluoroethoxy, heptafluorobutoxy, benzyloxy, fluorobenzyloxy, difluorobenzyloxy, trifluorobenzyloxy, amino, ethyl or methyl, nitro, cyano or chlorine,
$R^7$ and $R^8$ are identical and form, together with the nitrogen to which they are bonded, a pyrrolidine, morpholine, piperidine or piperazine ring, or denote hydrogen, methyl or ethyl.
$R^9$ denotes hydrogen,
Alkyl groups alone or as part of another group (for example alkoxy, alkoxycarbonyl, alkylmercapto, alkylsulfinyl, alkylsulfonyl, aralkyl or alkanoyl) are straight-chain or branched and are, for example, methyl, ethyl, n-propyl, isopropyl, isobutyl, sec-butyl, n-butyl, n-pentyl, isopentyl or n-hexyl.

Preferred $(C_1-C_6)$-alkoxy groups are methoxy or ethoxy.

Preferred $(C_1-C_6)$-alkoxycarbonyl groups are methoxycarbonyl or ethoxycarbonyl. $(C_6-C_{12})$-aryl-$(C_1-C_6)$-alkoxy is preferably understood to mean benzyloxy.

Preferred $(C_1-C_6)$-alkanoyl groups are formyl or acetyl.

Examples of $(C_3-C_8)$-cycloalkyl groups are cyclopropyl cyclobutyl, cyclopentyl and cyclohexyl, and preferred $(C_3-C_6)$-cycloalkyl groups are cyclopentyl or cyclohexyl.

Examples of aryl are phenyl, naphthyl or p-biphenylyl, and phenyl is preferred. Corresponding statements apply to radicals derived therefrom, such aralkyl, aryloxy, aralkyloxy and aroyl. $(C_1-C_9)$-Heteroaryl is defined as radicals of 5- or 6-membered monocyclic, or 9- or 10-membered bicyclic, heteroaromatic compounds having at least one carbon atom, 1 to 4 nitrogen atoms and/or 1 sulfur or oxygen atom as ring members, and are defined, for example, in Katritzky, Lagowski, Chemistry of the Heterocycles, Berlin, Heidelberg 1968, pages 3 to 5. Examples of monocyclic heteroaromatic compounds are thiophene, furan, pyrrole, imidazole, pyrazole, pyridine, tetrazole, pyrazine, pyrimidine, pyridazine, 1,2,4-triazole, thiazole, isothiazole, oxazole and isoxazole. Examples of bicyclic heteroaromatic compounds are benzothiophene, benzofuran, indole, isoindole, indazole, benzimidazole, quinoline, isoquinoline, phthalazine, quinoxaline, quinazpline and cinnoline.

Halogen is fluorine, chlorine, bromine or iodine. Fluorine and chlorine are preferred.

Particularly suitable salts are salts with physiologically tolerated acids and alkali metal and alkaline earth metal salts and salts with physiologically tolerated amines, which are formed by, for example, reaction with HCl, $H_2SO_4$, phosphoric acid, alicyclic, aromatic or heteroaromatic carboxylic or sulfonic acids, with methionine, tryptophan, lysine, arginine or the like.

$R^3$ preferably represents hydrogen, $(C_1-C_6)$-alkylcarbamoyl or a radical of the formula VI $$-(CO-O-)_p(CR^{11}R^{12}-O-)_q W-B \quad (VI)$$

in which p denotes 0 or 1, q denotes 0 or 1, W denotes a bond or —CO—, —$CR^{13}R^{14}$— or —CO—$CR^{13}R^{14}$—, and B denotes hydrogen, an acyl radical or an optionally substituted alkyl radical.

$R^{11}$ and $R^{12}$ are identical or different and denote hydrogen, $(C_1-C_6)$-alkyl, $(C_3-C_8)$-cycloalkyl, $(C_7-C_{11})$-aralkyl or $(C_6-C_{12})$-aryl.

B and $R^{11}$ can also together represent a —$[CH_2]_r$-chain with r=3, 4 or 5 - preferably 4 - it being possible for one hydrogen atom on each of one or more of the $CH_2$ groups to be replaced by OH, protected OH, amino, acylamino and/or halogen. A radical having a substituted —$[CH_2]_r$—chain is preferably a glycosyl radical which is, where appropriate, partially or completely protected with protective groups customary in carbohydrate chemistry and which is derived from a glycopyranose, glycofuranose or oligosaccharide.

Both α- and β-glycosidic linkage of the glycosyl radical is possible.

It can be, for example, a glycofuranosyl or glycopyranosyl radical derived from naturally occurring aldotetroses, aldopentoses, aldohexoses, ketopentoses, deoxyaldoses, aminoaldoses and oligosaccharides, such as di- and trisaccharides, as well as stereoisomers thereof.

These glycosyl radicals are derived, in particular, from natural D- or L-monosaccharides which occur in microorganisms, plants, animals or humans, such as ribose (Rib), arabinose (Ara), xylose (Xyl), lyxose (Lyx), allose (All), altrose (Alt), glucose (Glc), mannose (Man), gulose (Gul), idose (Ido), galactose (Gal), talose (Tal), erythrose (Ery), threose (Thr), psicose (Psi), fructose (Fru), sorbose (Sor), tagatose (Tag), xylulose (Xyu), fucose (Fuc), rhamnose (Rha), olivose (Oli), oliose (Olo), mycarose (Myc), rhodosamine (RN), N-acetylglucosamine (GlcNAc), N-acetylgalactosamine (GalNAc), N-acetylmannosamine (ManNAc) or disaccharides, such as maltose (Mal), lactose (Lac), cellobiose (Cel), gentibiose (Gen), N-acetyllactosamine (LacNAc), chitobiose (Chit), β-galactopyranosyl-(1->3)-N-acetylgalactosamine and the β-galactopyranosyl-(1->3)- or -(1->4)-N-acetylglucosamine, as well as synthetic derivatives thereof, such as 2-deoxy-, 2-amino-, 2-acetamido- or 2-halogeno-, preferably bromo- or iodo-, sugars.

Protective groups customary in carbohydrate chemistry are to be understood to be, for example, the $(C_1-C_{10})$-acyl protective groups such as $(C_1-C_6)$-alkanoyl (for example acetyl, trichloroacetyl and trifluoroacetyl), benzoyl or p-nitrobenzoyl, as well as optionally modified methyl, methyloxymethyl, benzyl, tetrahydropyranyl, benzylidene, isopropylidene or trityl groups, preference being given in this connection to the acyl protective groups, especially the acetyl (Ac) group.

(a) If p and q are 0, the radicals preferably have the following meanings:

W is a bond or denotes —CO—, —$CR^{13}R^{14}$— or —CO—$CR^{13}R^{14}$. B denotes hydrogen (only if W is not a bond), $(C_1-C_{10})$alkyl; $(C_2-C_{12})$-alkenyl; $(C_3-C_{12})$-cycloalkyl; $(C_6-C_{12})$-aryl which is optionally substituted by 1, 2 or 3 identical or different radicals from the series comprising $(C_1-C_4)$-alkyl, chlorine, bromine, fluorine, nitro, trifluoromethyl, $(C_1-C_4)$-alkoxy and hydroxyl; —$(CH_2)_s$—$CH(NH_2)$—$R^{15}$ with s=1-9; the acyl radical of an amino acid, or $(C_1-C_6)$-alkyl which is substituted by up to 4 identical or different radicals from the series comprising F, Cl or Br.

$R^{13}$ and $R^{14}$ are identical or different and denote hydrogen, $(C_1-C_6)$-alkyl, $(C_1-C_6)$-alkoxy, $(C_3-C_8)$cycloalkyl, $(C_7-C_{11})$-aralkyl, $(C_6-C_{12})$-aryl or pyridyl, or $R^{13}$ and $R^{14}$ together represent —[CH$_2$]$_4$—, —[CH$_2$]$_5$— or —[CH$_2$]$_6$—, in which 1 or 2 CH$_2$ groups can be replaced by O.

$R^{15}$ denotes hydrogen or $(C_1-C_{10})$-alkyl.

(b) If q is 1, W and B are as defined above under (a). Furthermore, W can denote —CO—O— and —CO—O—CR$^{13}$R$^{14}$—, with $R^{13}$ and $R^{14}$ having the abovementioned meanings. B can also represent hydrogen in the case where W=bond.

(c) If P is 1 and q is 0, W represents a bond or denotes —CR$^{13}$$^{R14}$—, with $R^{13}$ and $R^{14}$ having the meanings as under (a). B is defined as under (a) but cannot represent the acyl radical of an aminoacid. Furthermore, —CO—O—W—B can represent other N$^{im}$ protective groups which are of the urethane type but no embraced by the abovementioned definition (cf., for example, Hubbuch, Kontakte Merck 3/79 14–23; Bullesbach, Kontakte Merck 1/80 23–35).

An optionally substituted $(C_6-C_{12})$-aryl radical (see above under (a)) is to be understood to be, for example, phenyl, (o-, m-, p-)tolyl, (o-, m-, p-)ethylphenyl, 2-ethyltolyl, 4-ethyl-o-tolyl, 5-ethyl-m-tolyl, (o-, m- or p-)propylphenyl, 2-propyl-(m- or p-)tolyl, 4-isopropyl2,6-xylyl, 3-propyl-4-ethylphenyl, (2,3,4-, 2,3,6- or 2,4,5-)trimethylphenyl, (o-, m- or p-)fluorophenyl, (o-, m- or p-trifluoromethyl)phenyl, 4-fluoro-2,5-xylyl, (2,4-2,5-, 2,6-, 3,4- or 3,5-)difluorophenyl, (o-, m- or p-)chlorophenyl, 2-chloro-p-tolyl, (3-, 4-, 5- or 6-)chlorotolyl, 4-chloro-2-propylphenyl, 2-isopropyl-4-chlorophenyl, 4-chloro-3,5-xylyl, (2,3-, 2,4-, 2,5-, 2,6- or 3,5-)dichlorophenyl, 4-chloro-3-fluorophenyl, (3- or 4-)chloro-2-fluorophenyl, (o-, m- or p-)trifluoromethylphenyl, (o-, m- or p-)ethoxyphenyl, (4- or 5-)chloro-2-methoxyphenyl, 2,4-dichloro-(5- or 6-)methylphenyl or (o-, m- or p-)methoxyphenyl.

Examples of $(C_1-C_{10})$-alkyl are methyl, ethyl, propyl, butyl, pentyl, hexyl, heptyl, octyl, nonyl and decyl or their isomeric forms.

$(C_3-C_{12})$-cycloalkyl includes alkyl-substituted cycloalkyl and bi- and polycyclic systems. It is to be understood to include, for example: cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclophenyl, 2-pentylcyclopentyl, 3-tert-butylcyclopentyl, 2,2-dimethylcyclohexyl, cycloheptyl, cyclononyl, cyclodecyl, norbornyl or adamantyl.

An acyl radical of an amino acid is to be understood to be preferably the radical of an α-amino acid, in particular from the series of naturally occurring α-amino acids or their antipodes such as, for example, H-Gly-, H-Ala-, H-Val-, H-Leu-, H-Ile-, H-Phe-, H-Lys-, H-Pro-, H-Trp-, H-Met-, H-Ser-, H-Thr-, H-Cys-, H-Tyr-, H-Asn-, H-Gln-, H-Asp-, H-Glu-, H-Arg-, H-Orn- or the corresponding radicals in the D configuration.

Without intending to confine the subject matter of the invention thereto, some urethane protective groups $R^3=$—CO—O—WB according to the invention may be mentioned hereinafter: $(C_1-C_6)$-alkoxycarbonyl such as Boc; $(C_3-C_{12})$-cycloalkyloxycarbonyl such as Mboc, Iboc or Adoc;

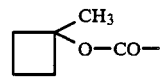
Mboc

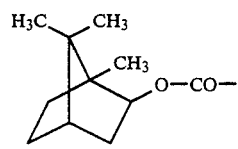
Iboc

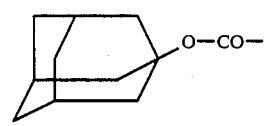
Adoc $(C_3-C_{12})$-cycloalkyl-$(C_1-C_6)$-alkoxycarbonyl such as Adpoc;

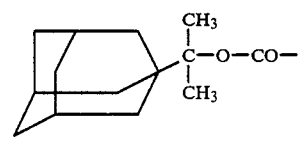
Adpoc $(C_6-C_{12})$-aryl-$(C_1-C_6)$-alkoxycarbonyl such as Z, Fmoc or Bpoc,

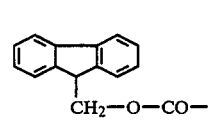
Fmoc

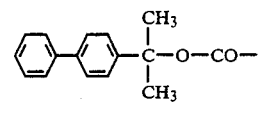
Bpoc substituted Z radicals such as Moc, Ddz and Z (p-NO$_2$)

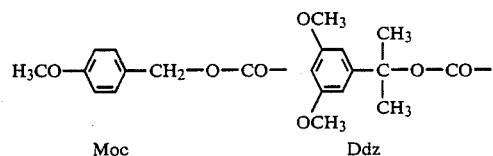
Moc          Ddz and modified Z radicals such as Pyoc and corresponding radicals derived from 2- and 3-picoline, all of which can be substituted as indicated above for $(C_6-C_{12})$-aryl.

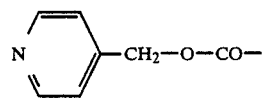
Pyoc

Preferred N$^{im}$ protective groups are those which can be eliminated in the presence of acids, preferably in a pH range of about 1–6 and/or under physiological conditions.

It is surprising that compounds of the formula I with $R^3 \neq H$ are more stable than the corresponding compounds with $R^3=H$. In particular, they are more stable under acid conditions as prevail, for example, in the stomach, and in the presence of water. Thus, it is possible for the expert, by specific choice of an N$^{im}$ protective group, to control the release of the active compounds in such a way that this takes place selectively at the site of action.

Any chiral carbon and sulfur atoms present can occur both in the R and in the S configuration. In such cases, compounds of the formula I exist in the form of the pure enantiomers or as a stereoisomer mixture (such as enantiomer mixture and diastereomer mixture).

The following compounds are of particular importance:

2-[4-Pyrrolidino-2-pyrimidinylmethylsulfinyl]-1H-thieno[3,4-d]imidazole,
2-[4-Piperidino-2-pyrimidinylmethylsulfinyl]-1H-thieno[3,4-d]imidazole,
2-[4-Morpholino-2-pyrimidinylmethylsulfinyl]-1H-thieno[3,4-d]imidazole,
2-[4-(N,N-Dimethylamino)-2-pyrimidinylmethylsulfinyl]-1H-thieno[3,4-d]imidazole,
2-[5-Methyl-4-pyrrolidino-2-pyrimidinylmethylsulfinyl]-1H-thieno[3,4-d]imidazole,
2-[5-Methyl-4-piperidino-2-pyrimidinylmethylsulfinyl]-1H-thieno[3,4-d]imidazole,
2-[5-Methyl-4-morpholino-2-pyrimidinylmethylsulfinyl]-1H-thieno[3,4-d]imidazole,
2-[5-Methyl-4-(N,N-dimethylamino)-2-pyrimidinylmethylsulfinyl]-1H-thieno[3,4-d]imidazole,
2-[5-Amino-4-pyrrolidino-2-pyrimidinylmethylsulfinyl]-1H-thieno[3,4-d]imidazole,
2-[5-Amino-4-piperidino-2-pyrimidinylmethylsulfinyl]-1H-thieno[3,4-d]imidazole,
2-[5-Amino-4-morpholino-2-pyrimidinylmethylsulfinyl]-1H-thieno[3,4-d]imidazole,
2-[5-Amino-4-(N,N-dimethylamino)-2-pyrimidinylmethylsulfinyl]-1H-thieno[3,4-d]imidazole,
2-[5-Chloro-4-pyrrolidino-2-pyrimidinylmethylsulfinyl]-1H-thieno[3,4-d]imidazole,
2-[5-Chloro-4-piperidino-2-pyrimidinylmethylsulfinyl]-1H-thieno[3,4-d]imidazole,
2-[5-Chloro-4-morpholino-2-pyrimidinylmethylsulfinyl]-1H-thieno[3,4-d]imidazole,
2-[5-Chloro-4-(N,N-dimethylamino)-2-pyrimidinylmethylsulfinyl]-1H-thieno[3,4-d]imidazole,
2-[5-Chloro-6-pyrrolidino-4-pyrimidinylmethylsulfinyl]-1H-thieno[3,4-d]imidazole,
2-[5-Chloro-6-piperidino-4-pyrimidinylmethylsulfinyl]-1H-thieno[3,4-d]imidazole,
2-[5-Chloro-6-morpholino-4-pyrimidinylmethylsulfinyl]-1H-thieno[3,4-d]imidazole,
2-[5-Chloro-6-(N,N-dimethylamino)-4-pyrimidinylmethylsulfinyl]-1H-thieno[3,4-d]imidazole,
2-[6-Pyrrolidino-4-pyrimidinylmethylsulfinyl]-1H-thieno[3,4-d]imidazole,
2-[6-Piperidino-4-pyrimidinylmethylsulfinyl]-1H-thieno[3,4-d]imidazole,
2-[6-Morpholino-4-pyrimidinylmethylsulfinyl]-1H-thieno[3,4-d]imidazole,
2-[6-(N,N-Dimethylamino)-4-pyrimidinylmethylsulfinyl]-1H-thieno[3,4-d]imidazole,
2-[5-Methyl-6-pyrrolidino-4-pyrimidinylmethylsulfinyl]-1H-thieno[3,4-d]imidazole,
2-[5-Methyl-6-piperidino-4-pyrimidinylmethylsulfinyl]-1H-thieno[3,4-d]imidazole,
2-[5-Methyl-6-morpholino-4-pyrimidinylmethylsulfinyl]-1H-thieno[3,4-d]imidazole,
2-[5-Methyl-6-(N,N-dimethylamino)-4-pyrimidinylmethylsulfinyl]-1H-thieno[3,4-d]imidazole,
2-[5-Amino-6-pyrrolidino-4-pyrimidinylmethylsulfinyl]-1H-thieno[3,4-d]imidazole,
2-[5-Amino-6-piperidino-4-pyrimidinylmethylsulfinyl]-1H-thieno[3,4-d]imidazole,
2-[5-Amino-6-morpholino-4-pyrimidinylmethylsulfinyl]-1H-thieno[3,4-d]imidazole,
2-[5-Methoxy-6-(N,N-dimethylamino)-4-pyrimidinylmethylsulfinyl]-1H-thieno[3,4-d]imidazole,
2-[4-Methyl-2-pyrimidinylmethylsulfinyl]-1H-thieno[3,4-d]imidazole,
2-[4-Ethoxy-2-pyrimidinylmethylsulfinyl]-1H-thieno[3,4-d]imidazole,
2-[4-Benzyloxy-2-pyrimidinylmethylsulfinyl]-1H-thieno[3,4-d]imidazole,
2-[4-Phenoxy-2-pyrimidinylmethylsulfinyl]-1H-thieno[3,4-d]imidazole,
2-[4-Isopropoxy-2-pyrimidinylmethylsulfinyl]-1H-thieno[3,4-d]imidazole,
2-[4-Methoxy-5-methyl-2-pyrimidinylmethylsulfinyl]-1H-thieno[3,4-d]imidazole,
2-[4-Ethoxy-5-methyl-2-pyrimidinylmethylsulfinyl]-1H-thieno[3,4-d]imidazole,
2-[4-Benzyloxy-5-methyl-2-pyrimidinylmethylsulfinyl]-1H-thieno[3,4-d]imidazole,
2-[5-Methyl-4-phenoxy-2-pyrimidinylmethylsulfinyl]-1H-thieno[3,4-d]imidazole,
2-[4-Isopropoxy-5-methyl-2-pyrimidinylmethylsulfinyl]-1H-thieno[3,4-d]imidazole,
2-[5-Chloro-4-methoxy-2-pyrimidinylmethylsulfinyl]-1H-thieno[3,4-d]imidazole,
2-[5-Chloro-4-ethoxy-2-pyrimidinylmethylsulfinyl]-1H-thieno[3,4-d]imidazole,
2-[5-Chloro-4-isopropoxy-2-pyrimidinylmethylsulfinyl]-1H-thieno[3,4-d]imidazole,
2-[4-Benzyloxy-5-chlor-2-pyrimidinylmethylsulfinyl]-1H-thieno[3,4-d]imidazole,
2-[5-Chloro-4-phenoxy-2-pyrimidinylmethylsulfinyl]-1H-thieno[3,4-d]imidazole,
2-[6-Methoxy-4-pyrimidinylmethylsulfinyl]-1H-thieno[3,4-d]imidazole,
2-[6-Ethoxy-4-pyrimidinylmethylsulfinyl]-1H-thieno[3,4-d]imidazole,
2-[6-Benzyloxy-4-pyrimidinylmethylsulfinyl]-1H-thieno[3,4-d]imidazole,
2-[6-Methoxy-5-methyl-4-pyrimidinylmethylsulfinyl]-1H-thieno[3,4-d]imidazole,
2-[6-Ethoxy-5-methyl-4-pyrimidinylmethylsulfinyl]-1H-thieno[3,4-d]imidazole,
2-[5-Benzyloxy-5-methyl-4-pyrimidinylmethylsulfinyl]-1H-thieno[3,4-d]imidazole,
2-[5-Chloro-6-methoxy-4-pyrimidinylmethylsulfinyl]-1H-thieno[3,4-d]imidazole,
2-[5-Chloro-6-ethoxy-4-pyrimidinylmethylsulfinyl]-1H-thieno[3,4-d]imidazole,
2-[4-Methylthio-2-pyrimidinylmethylsulfinyl]-1H-thieno[3,4-d]imidazole,
2-[4-Ethylthio-2-pyrimidinylmethylsulfinyl]-1H-thieno[3,4-d]imidazole,
2-[5-Methyl-4-methylthio-2-pyrimidinylmethylsulfinyl]-1H-thieno[3,4-d]imidazole,
2-[5-Methyl-4-ethylthio-2-pyrimidinylmethylsulfinyl]-1H-thieno[3,4-d]imidazole,
2-[5-Chloro-4-methylthio-2-pyrimidinylmethylsulfinyl]-1H-thieno[3,4-d]imidazole,
2-[5-Chloro-4-ethylthio-2-pyrimidinylmethylsulfinyl]-1H-thieno[3,4-d]imidazole,
2-[6-Methylthio-4-pyrimidinylmethylsulfinyl]-1H-thieno[3,4-d]imidazole, 2-[6-Ethylthio-4-pyrimidinylmethylsulfinyl]-1H-thieno[3,4-d]imidazole,
2-[5-Methyl-6-methylthio-4-pyrimidinylmethylsulfinyl]-1H-thieno[3,4-d]imidazole,
2-[6-Ethylthio-5-methyl-4-pyrimidinylmethylsulfinyl]-1H-thieno[3,4-d]imidazole,
2-[5-Chloro-6-methylthio-4-pyrimidinylmethylsulfinyl]-1H-thieno[3,4-d]imidazole,
2-[5-Chloro-6-ethylthio-4-pyrimidinylmethylsulfinyl]-1H-thieno[3,4-d]imidazole,
2-(5-Trifluormethyl-4-pyrrolidino-2-pyrimidinylmethylsulfinyl)-1H-thieno[3,4-d]imidazole,
2-(5-Trifluormethyl-4-piperidino-2-pyrimidinylmethylsulfinyl)-1H-thieno[3,4-d]imidazole,
2-(5-Trifluormethyl-4-morpholino-2-pyrimidinylmethylsulfinyl)-1H-thieno[3,4-d]imidazole,
2-[5-Trifluormethyl-4-(N,N-dimethylamino)-2-pyrimidinylmethylsulfinyl]-1H-thieno[3,4-d]imidazole,
2-(5-Fluoro-4-pyrrolidino-2-pyrimidinylmethylsulfinyl)-1H-thieno[3,4-d]imidazole,
2-(5-Fluoro-4-pyrrolidino-2-pyrimidinylmethylsulfinyl)-1H-thieno[3,4-d]imidazole,
2-(5-Fluoro-4-morpholino-2-pyrimidinylmethylsulfinyl)-1H-thieno[3,4-d]imidazole,
2-[5-Fluoro-4-(N,N-dimethylamino)-2-pyrimidinylmethylsulfinyl]-1H-thieno[3,4-d]imidazole,
2-(5-Cyano-4-pyrrolidino-2-pyrimidinylmethylsulfinyl)-1H-thieno[3,4-d]imidazole,
2-(5-Cyano-4-piperidino-2-pyrimidinylmethylsulfinyl]-1H-thieno[3,4-d]imidazole,
2-(5-Fluoro-6-pyrrolidino-4-pyrimidinylmethylsulfinyl)-1H-thieno[3,4-d]imidazole,
2-(5-Fluoro-6-piperidino-4-pyrimidinylmethylsulfinyl)-1H-thieno[3,4-d]imidazole,
2-(5-Fluoro-6-morpholino-4-pyrimidinylmethylsulfinyl)-1H-thieno[3,4-d]imidazole,
2-[5-Fluoro-6-(N,N-dimethylamino)-4-pyrimidinylmethylsulfinyl]-1H-thieno[3,4-d]imidazole,
2-(5-Cyano-6-pyrrolidino-4-pyrimidinylmethylsulfinyl]-1H-thieno[3,4-d]imidazole,
2-(5-Cyano-6-piperidino-4-pyrimidinylmethylsulfinyl]-1H-thieno[3,4-d]imidazole,
2-(5-Cyano-6-morpholino-4-pyrimidinylmethylsulfinyl)-1H-thieno[3,4-d]imidazole,
2-[5-Cyano-6-(N,N-dimethylamino)-4-pyrimidinylmethylsulfinyl]-1H-thieno[3,4-d]imidazole,
2-(5-Nitro-6-pyrrolidino-4-pyrimidinylmethylsulfinyl)-1H-thieno[3,4-d]imidazole,
2-(5-Nitro-6-piperidino-4-pyrimidinylmethylsulfinyl)-1H-thieno[3,4-d]imidazole,
2-(5-Nitro-6-morpholino-4-pyrimidinylmethylsulfinyl)-1H-thieno[3,4-d]imidazole,
2-[5-Nitro-6-(N,N-dimethylamino)-4-pyrimidinylmethylsulfinyl]-1H-thieno[3,4-d]imidazole,
2-(5-Cyano-4-morpholino-2-pyrimidinylmethylsulfinyl)-1H-thieno[3,4-d]imidazole,
2-[5-Cyano-4-N,N-dimethylamino)-2-pyrimidinylmethylsulfinyl]-1H-thieno[3,4-d]imidazole,
2-(5-Nitro-4-pyrrolidino-2-pyrimidinylmethylsulfinyl)-1H-thieno[3,4-d]imidazole,
2-(5-Nitro-4-piperidino-2-pyrimidinylmethylsulfinyl)-1H-thieno[3,4-d]imidazole,
2-(5-Nitro-4-morpholino-2-pyrimidinylmethylsulfinyl)-1H-thieno[3,4-d]imidazole,
2-[5-Nitro-4-(N,N-dimethylamino)-2-pyrimidinylmethylsulfinyl]-1H-thieno[3,4-d]imidazole,
2-(5-Trifluormethyl-6-pyrrolidino-4-pyrimidinylmethylsulfinyl)-1H-thieno[3,4-d]imidazole,
2-(5-Trifluormethyl-6-piperidino-4-pyrimidinylmethylsulfinyl)-1H-thieno[3,4-d]imidazole,
2-(5-Trifluormethyl-6-morpholino-4-pyrimidinylmethylsulfinyl)-1H-thieno[3,4-d]imidazole,
2-[5-Trifluormethyl-6-(N,N-dimethylamino)-4-pyrimidinylmethylsulfinyl]-1H-thieno[3,4-d]imidazole, The invention also relates to a process for the preparation of compounds of the formula I, which comprises (a) reaction of a compound of the formula II

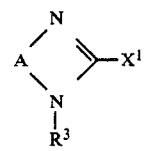

(II)

in which A, $R^1$, $R^2$ and $R^3$ are as defined on pages 1 and 2 and $X^1$ denotes i. a leaving group or ii. —SH, —S$^-$M$^+$ or —SO$_2^-$M$^+$, with M$^+$ representing a cation, for example an alkali or alkaline earth metal, ammonium or alkylammonium ion, in particular a sodium or potassium ion, with a compound of the formula III

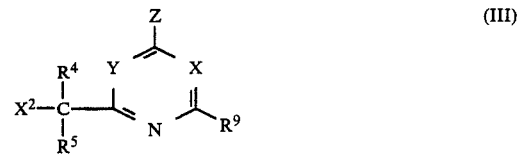

(III)

in which X, Y, Z, $R^4$, $R^5$, $R^6$, $R^7$, $R^8$, $R^9$ and $R^{10}$ are as defined on pages 2 and 3, and $X^2$ denotes —SH, —S$^-$M$^+$ or —SO$_2^-$M$^+$, with M$^+$ representing a cation in the abovementioned case i. and denotes a leaving group in the abovementioned case ii. or (b) reaction of a compound of the formula IV

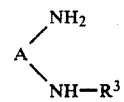

(IV)

in which A, $R^1$, $R^2$ and $R^3$ are as defined above, with a compound of the formula V

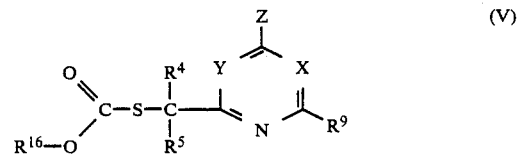

(V)

in which X, Y, Z, $R^4$, $R^5$, $R^6$, $R^7$, $R^8$, $R^9$ and $R^{10}$ are as defined above, and $R^{16}$ represents an esterifying group, i. if desired, oxidation of (an) —S— group(s) present where appropriate in a compound of the formula I to (an) —SO— or —SO$_2$— group(s), ii. if desired, oxidation of (an) —SO— group(s) present where appropriate in a compound of the formula I to (an) —SO$_2$— group(s), iii. if desired, acylation, alkylation or aralkylation of a compound of the formula I in which R$^3$ represents hydrogen, iv. if desired, hydrolysis of a compound of the formula I in which R$^3$ does not denote hydrogen, and v. conversion of a compound of the formula I, if desired, into its physiologically tolerated salt, it also being possible for two or more of the measures i.–iv. to be carried out in a sequence other than that indicated.

If, in accordance with the process variant (a) which is preferred here, compounds of the formula II are reacted with compounds of the formula III, then X$^1$ or X$^2$ represents a leaving group which can be detached nucleophilically, such as Cl, Br, I, —O—SO$_2$—CH$_3$, —O—SO$_2$—CF$_3$ or —O—SO$_2$—(C$_6$H$_4$—pCH$_3$).

The reaction of a compound of the formula II with a compound of the formula III or salts thereof is carried out in an inert solvent such as, for example, water, methylene chloride, methanol, ethanol, acetone, ethyl acetate, toluene, tetrahydrofuran, acetonitrile, dimethylformamide, dimethyl sulfoxide or mixtures of these solvents, expediently in the presence of an inorganic or organic base such as, for example, the hydroxide, carbonate, alkoxide, hydride or amide of sodium or potassium, or ammonia, triethylamine, tributylamine or pyridine, at −20° to +150° C., preferably at 0°–80° C.

The compounds of the formula II can be prepared in analogy to known processes, for example by ring closure of appropriately substituted 2,3-, 3,4- or 4,5-diaminothiophenes of the formula IV defined above using appropriate sulfur compounds such as carbon disulfide (for example DE-A 3,132,167).

The 2,3-, 3,4- or 4,5-diaminothiophenes required for this are either known from the literature or can be prepared in analogy to known processes. They are obtained by, for example, reduction of appropriately substituted aminonitrothiophenes.

R$^{16}$ in the esters of the formula V used in process variant (b) represents an esterifying group, preferably (C$_1$–C$_6$)-alkyl or benzyl.

The reaction of a compound of the formula IV with a compound of the formula V in process variant (b) is carried out in analogy to the procedures described in Preston et al., Benzimidazoles and Congeneric Tricyclic Compounds, Part 1, New York, pages 10–13.

The compounds of the formula I obtained in this way can, if R$^3$ denotes hydrogen, be converted into physiologically tolerated salts.

Furthermore, compounds of the formula I with T=—S— can be converted, using suitable oxidizing agents, into those with T=—SO— or —SO$_2$—. It is also possible in the same way to oxidize —S— groups in the substituents R$^1$, R$^2$ and R$^6$ to R$^9$.

This reaction is carried out in a suitable inert solvent such as, for example, methylene chloride, chloroform, carbon tetrachloride, 1,2-dichloroethane, toluene, ethyl acetate, acetic acid, trifluoroacetic acid, water, methanol, ethanol or mixtures thereof, at −20° C. to +150° C., preferably at −10° C. to +40° C.

Examples of suitable oxidizing agents are: hydrogen peroxide, peracids and peresters such as peracetic acid, trifluoroperacetic acid, monoperphthalic acid, m-chloroperbenzoic acid and esters thereof, ozone, dinitrogen tetroxide, iodosobenzene, N-chlorosuccinimide, 1-chlorobenzotriazole, sodium hypochlorite, potassium peroxodisulfate, t-butyl hypochlorite, tetrabutylammonium periodate or permanganate, sodium metaperiodate, selenium dioxide or manganese dioxide, ceric ammonium nitrate, chromic acid, chlorine, bromine, diazabicyclo[2.2.2]octane/bromine complex, dioxane dibromide, pyridinium bromide perbromide, sulfuryl chloride, 2-arylsulfonyl-3-aryloxaziridines, titanium tetraisopropylate/tert-butyl hydroperoxide (where appropriate with the addition of dialkyl esters of (D)- or (L)-tartaric acid and a defined amount of water).

It is likewise possible to use isolated, where appropriate immobilized, oxidizing enzymes or microorganisms as oxidizing agents.

The oxidizing agents are used in equimolar amounts or, where appropriate, in a small excess of 5–10 mol-% in the oxidation to T=—SO—, or in larger excess and/or at higher reaction temperature when oxidation to T=—SO$_2$— is desired.

Compounds of the formula I with R$^3\neq$H can be prepared starting from compounds of the formula IV with R$^3\neq$H and compounds of the formula V, or by acylation, alkylation or aralkylation of compounds of the formula I with R$^3$=H. The second route will be dealt with in somewhat more detail hereinafter.

The acylation, alkylation or aralkylation of compounds of the formula I is carried out in a manner known per se using the appropriate acylating agents, alkylating agents or aralkylating agents in a suitable organic solvent, as a rule at a temperature between −78° C. and the boiling point of the reaction mixture, where appropriate in the presence of a base.

N$^{im}$ protective groups of the formula VI with p=0, q=1, W=bond and B=hydrogen can be introduced into compounds of the formula I (R$^3$=H, T=S) by, for example, hydroxyalkylation, it being possible to introduce N$^{im}$ protective groups with R$^{11}$=R$^{12}$=hydrogen in a manner known per se (cf., for example, Eur. J. Med. Chem. 15 [1980]586; J. Med. Chem. 22 [1979]1113) by hydroxymethylation using formaldehyde in an organic solvent such as, for example, acetonitrile. The hydroxyalkylation is carried out at a temperature between 0° C. and the boiling point of the reaction mixture, where appropriate in the presence of a base such as triethylamine.

Hydroxymethyl compounds of the formula VII

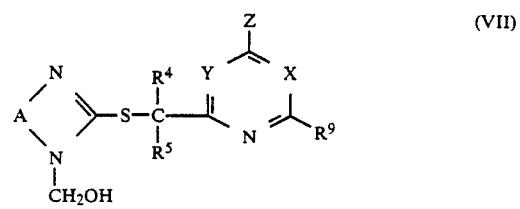

can be converted in the manner described in EP-A No. 176,308, page 11, into acyl derivatives of the formula VIII

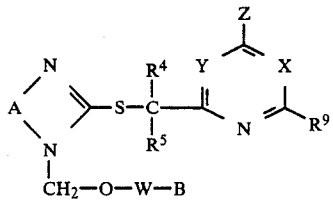

(VIII)

in which W-B is an acyl radical.

Compounds of the formula I with $R^3=H$ can also be alkylated with reagents of the formula IX

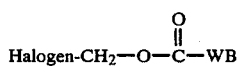

(IX)

such as, for example, chloromethyl pivalate, in a known manner, resulting in the corresponding carbonates (W=—CO—O— or —CO—O—$CR^{13}R^{14}$—). The reaction is carried out, for example, in the manner described in EP-A No. 176,308, page 12.

Acyl radicals of amino acids are coupled in a known manner, for example DCC/HOBt or dialkylphosphinic anhydride method) to compounds of the formula I with $R^3=H$.

$N^{im}$ protective groups of the formula VI with p=0, q=1 and $R^{11}$ and/or $R^{12} \neq$ hydrogen are introduced by reacting a compound of the formula I ($R^3=H$, $T=S$) with 1 to 10 equivalents, preferably 2 to 3 equivalents, of the appropriate α-halogenoalkyl ester. The α-halogenoalkyl esters used are obtained from acid halides and aldehydes by known methods (cf., for example J. Amer. Chem. Soc. 43 [1921]660; J. Med. Chem. 23 [1980]469-474).

Bromoalkyl esters are preferably used. Alternatively, it is possible to treat the anion of a compound of the formula I ($R^3=H$, $T=S$), which can be obtained from the latter and NaH, with the α-halogenoalkyl ester.

It is also possible, in place of the α-halogenoalkyl esters, to use [1-(alkylcarbonyloxy)alkyl]pyridinium salts which are prepared in analogy to the known [1-(arylcarbonyloxy)alkyl]pyridinium salts (cf. Angew. Chem. Suppl. 1982, 675-685) from the corresponding acyl halides, aldehydes and pyridine.

Alkylamino acetals of the formula I in which $R^3$ represents a radical of the formula VI in which p is 0, q is 1 and W denotes a bond or —$CR^{13}R^{14}$—, and B has the above meaning, are prepared by treating a compound of the abovementioned formula VI in a dipolar aprotic solvent, such as dimethylformamide, with about one equivalent of NaH at about 20° to 50° C., preferably at about 25° C. The resulting anion is then reacted with about one equivalent of a halogeno ether of the formula halogen—$CR^{11}R^{12}$—W—B (halogen=chlorine or bromine), the reaction mixture being stirred at about 20° to 50° C., preferably at about 25° C., for 15 minutes. The halogeno ethers are known and many of them are commercially available, or they can be prepared in analogy to known compounds.

Urethanes of the formula I in which $R^3$ represents a urethane protective group of the formula VI (p=1, q=0 and W=bond or —$CR^{13}R^{14}$—) are obtained from the corresponding compounds with $R^3=H$ by reacting the latter, where appropriate in the presence of a base such as NaH, in a suitable solvent such as DMF, with fluoro- or chloroformic esters of the formula Cl(F)-CO-O-WB-(in analogy to the procedure described in EP-A No. 176,308, page 12).

The fluoro- and chloroformates are known, and they are often commercially available or can be prepared by known methods.

Aralkyloxycarbonyl and alkoxycarbonyl groups can also be introduced using the known dicarbonates, which can often be bought, such as di-tert.-butyl dicarbonate and dibenzyl dicarbonate.

Substituted or modified Z groups in which $R^{13}$ and/or $R^{14}$ are hydrogen are prepared by reaction of the corresponding unprotected compound of the formula I, if necessary with the assistance of a base, with the appropriate azides or the appropriate carbonates.

The processes which can be used for the acylation of the compounds of the formula I ($R^3=H$, $T=S$) besides the customary standard conditions (for example acetic anhydride, triethylamine, dimethylaminopyridine) are others such as, for example, reaction with N-[1-(arylcarbonyloxy)alkyl]pyridinium salts (disclosed in Angew. Chem. Suppl. 1982, 675-685).

For the preparation of dialkoxy derivatives of the formula I ($R^3=$—$CR^{13}R^{14}$—B, in which $R^{13}$ and $R^{14}$ each denotes alkoxy, or together denote alkylenedioxy, and B denotes H; T=S or SO) a corresponding compound of the formula I with $R^3=H$ is preferably reacted in the presence of a base with the appropriate orthoformic esters such as trialkyl orthoformates.

Compounds of the formula III in which $X^2$ is hydroxyl can be prepared by reaction of appropriately substituted amidines with suitably substituted β-keto esters. For example, reaction of methoxyacetamidine hydrochloride with the sodium salt of ethyl formylacetate yields the compound of the formula III (Y=N, X=CH, $X^2=OCH_3$, Z=OH). The reaction of formamidine acetate with methyl 3-keto-4-methoxybutyrate analogously results in the compound of the formula III (Y=CH, X=N, $X^2=OCH_3$, Z=OH).

Apart from the thienoimidazole derivatives described in the examples, it is possible according to the invention also to obtain, for example, the compounds of the general formula I or the salts thereof which are listed in the table which follows.

Abbreviations used:

methyl (Me), ethyl (Et), propyl (Pr), Butyl (Bu), hexyl (Hex), acetyl (Ac), phenyl (Ph), cyclo (c), iso (i).

TABLE

| (T = SO; A as defined above under (b); $R^4$; $R^5$ and $R^9$ each = hydrogen) | | | | | | | |
|---|---|---|---|---|---|---|---|
| $R^1$ | $R^2$ | $R^3$ | $R^6$ | X | Y | Z | $R^{10}$ |
| Me | Me | H | Cl | N | $CR^6$ | $OR^{10}$ | Me |
| Me | Me | H | Cl | N | $CR^6$ | $OR^{10}$ | Et |
| Me | Me | H | Cl | N | $OR^6$ | $OR^{10}$ | i-Pr |
| Me | Me | H | Cl | N | $OR^6$ | $OR^{10}$ | $CH_2Ph$ |
| Me | Me | H | Cl | N | $OR^6$ | $OR^{10}$ | Ph |
| Me | Me | H | Cl | $OR^6$ | N | $OR^{10}$ | Me |
| Me | Me | H | Cl | $OR^6$ | N | $OR^{10}$ | Et |
| Me | Me | H | Cl | $OR^6$ | N | $OR^{10}$ | i-Pr |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| Me | Me | H | Cl | $OR^6$ | N | $OR^{10}$ | $CH_2Ph$ |
| Me | Me | H | Cl | $OR^6$ | N | $OR^{10}$ | Ph |
| Me | Me | H | $CH_3$ | N | $CR^6$ | $OR^{10}$ | Me |
| Me | Me | H | $CH_3$ | N | $CR^6$ | $OR^{10}$ | Et |
| Me | Me | H | $CH_3$ | N | $CR^6$ | $OR^{10}$ | i-Pr |
| Me | Me | H | $CH_3$ | N | $CR^6$ | $OR^{10}$ | Ph |
| Me | Me | H | $CH_3$ | N | $CR^6$ | $OR^{10}$ | $CH_2Ph$ |
| Me | Me | H | Me | $CR^6$ | N | $OR^{10}$ | Me |
| Me | Me | H | Me | $CR^6$ | N | $OR^{10}$ | Et |
| Me | Me | H | Me | $CR^6$ | N | $OR^{10}$ | i-Pr |
| Me | Me | H | Me | $CR^6$ | N | $OR^{10}$ | $CH_2Ph$ |
| Me | Me | H | Me | $CR^6$ | N | $OR^{10}$ | Ph |
| Me | Me | H | H | $CR^6$ | N | $OR^{10}$ | Me |
| Me | Me | H | H | $CR^6$ | N | $OR^{10}$ | Et |
| Me | Me | H | H | $CR^6$ | N | $OR^{10}$ | i-Pr |
| Me | Me | H | H | $CR^6$ | N | $OR^{10}$ | $CH_2Ph$ |
| Me | Me | H | H | $CR^6$ | N | $OR^{10}$ | Ph |
| Me | Me | H | H | N | $CR^6$ | $OR^{10}$ | Me |
| Me | Me | H | H | N | $CR^6$ | $OR^{10}$ | Et |
| Me | Me | H | H | N | $CR^6$ | $OR^{10}$ | i-Pr |
| Me | Me | H | H | N | $CR^6$ | $OR^{10}$ | $Ch_2Ph$ |
| Me | Me | H | H | N | $CR^6$ | $OR^{10}$ | Ph |
| H | H | H | Cl | $CR^6$ | N | $OR^{10}$ | Me |
| H | H | H | Cl | $CR^6$ | N | $OR^{10}$ | Et |
| H | H | H | Cl | $CR^6$ | N | $OR^{10}$ | i-Pr |
| H | H | H | Cl | $CR^6$ | N | $OR^{10}$ | $CH_2Ph$ |
| H | H | H | Cl | $CR^6$ | N | $OR^{10}$ | Ph |
| H | H | H | Cl | N | $CR^6$ | $OR^{10}$ | Me |
| H | H | H | Cl | N | $CR^6$ | $OR^{10}$ | Et |
| H | H | H | Cl | N | $CR^6$ | $OR^{10}$ | i-Pr |
| H | H | H | Cl | N | $CR^6$ | $OR^{10}$ | $CH_2Ph$ |
| H | H | H | Cl | N | $CR^6$ | $OR^{10}$ | Ph |
| H | H | H | H | $CR^6$ | N | $OR^{10}$ | Me |
| H | H | H | H | $CR^6$ | N | $OR^{10}$ | Et |
| H | H | H | H | $CR^6$ | N | $OR^{10}$ | i-Pr |
| H | H | H | H | $CR^6$ | N | $OR^{10}$ | $CH_2Ph$ |
| H | H | H | H | $CR^6$ | N | $OR^{10}$ | Ph |
| H | H | H | H | N | $CR^6$ | $OR^{10}$ | Me |
| H | H | H | H | N | $CR^6$ | $OR^{10}$ | Et |
| H | H | H | H | N | $CR^6$ | $OR^{10}$ | i-Pr |
| H | H | H | H | N | $CR^6$ | $OR^{10}$ | $CH_2Ph$ |
| H | H | H | H | N | $CR^6$ | $OR^{10}$ | Ph |
| Me | Me | H | Me | N | $CR^6$ | $SR^{10}$ | H |
| Me | Me | H | Me | N | $CR^6$ | $SR^{10}$ | Me |
| Me | Me | H | Me | N | $CR^6$ | $SR^{10}$ | Et |
| Me | Me | H | Me | N | $CR^6$ | $SR^{10}$ | i-Pr |
| Me | Me | H | Me | N | $CR^6$ | $SR^{10}$ | Ph |
| Me | Me | H | Me | $CR^6$ | N | $SR^{10}$ | H |
| Me | Me | H | Me | $CR^6$ | N | $SR^{10}$ | Me |
| Me | Me | H | Me | $CR^6$ | N | $SR^{10}$ | Et |
| Me | Me | H | Me | $CR^6$ | N | $SR^{10}$ | i-Pr |
| Me | Me | H | Me | $CR^6$ | N | $SR^{10}$ | Ph |
| H | H | H | Me | N | $CR^6$ | $SR^{10}$ | H |
| H | H | H | Me | N | $CR^6$ | $SR^{10}$ | Me |
| H | H | H | Me | N | $CR^6$ | $SR^{10}$ | Et |
| H | H | H | Me | N | $CR^6$ | $SR^{10}$ | i-Pr |
| H | H | H | Me | N | $CR^6$ | $SR^{10}$ | Ph |
| H | H | H | Me | $CR^6$ | N | $SR^{10}$ | H |
| H | H | H | Me | $CR^6$ | N | $SR^{10}$ | Me |
| H | H | H | Me | $CR^6$ | N | $SR^{10}$ | Et |
| H | H | H | Me | $CR^6$ | N | $SR^{10}$ | i-Pr |
| H | H | H | Me | $CR^6$ | N | $SR^{10}$ | Ph |
| H | H | H | H | N | $CR^6$ | $SR^{10}$ | H |
| H | H | H | H | N | $CR^6$ | $SR^{10}$ | Me |
| H | H | H | H | N | $CR^6$ | $SR^{10}$ | Et |
| H | H | H | H | N | $CR^6$ | $SR^{10}$ | i-Pr |
| H | H | H | H | N | $CR^6$ | $SR^{10}$ | Ph |
| H | H | H | H | $CR^6$ | N | $SR^{10}$ | H |
| H | H | H | H | $CR^6$ | N | $SR^{10}$ | Me |
| H | H | H | H | $CR^6$ | N | $SR^{10}$ | Et |
| H | H | H | H | $CR^6$ | N | $SR^{10}$ | i-Pr |
| H | H | H | H | $CR^6$ | N | $SR^{10}$ | Ph |
| Me | Me | H | H | N | $CR^6$ | $SR^{10}$ | H |
| Me | Me | H | H | N | $CR^6$ | $SR^{10}$ | Me |
| Me | Me | H | H | N | $CR^6$ | $SR^{10}$ | Et |
| Me | Me | H | H | N | $CR^6$ | $SR^{10}$ | i-Pr |
| Me | Me | H | H | N | $CR^6$ | $SR^{10}$ | Ph |
| Me | Me | H | H | $CR^6$ | N | $SR^{10}$ | H |
| Me | Me | H | H | $CR^6$ | N | $SR^{10}$ | Me |
| Me | Me | H | H | $CR^6$ | N | $SR^{10}$ | Et |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| Me | Me | H | H | $CR^6$ | N | $SR^{10}$ | i-Pr |
| Me | Me | H | H | $CR^6$ | N | $SR^{10}$ | Ph |
| H | H | H | H | $CR^6$ | N | —$NH_2$ | |
| H | H | H | H | $CR^6$ | N | —NHMe | |
| H | H | H | H | $CR^6$ | N | —NHEt | |
| H | H | H | H | $CR^6$ | N | —NHPh | |
| H | H | H | H | $CR^6$ | N | —NH—$CH_2$Ph | |
| H | H | H | H | $CR^6$ | N | 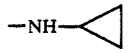 | |
| H | H | H | H | $CR^6$ | N | —NH-i-Pr | |
| H | H | H | H | $CR^6$ | N | 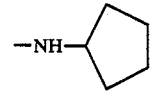 | |
| H | H | H | H | $CR^6$ | N | 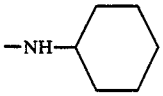 | |
| H | H | H | H | $CR^6$ | N | —$NMe_2$ | |
| H | H | H | H | $CR^6$ | N | —$NEt_2$ | |
| H | H | H | H | $CR^6$ | N | —$N(iPr)_2$ | |
| H | H | H | H | $CR^6$ | N | 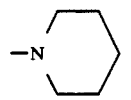 | |
| H | H | H | H | $CR^6$ | N | 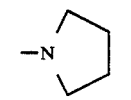 | |
| H | H | H | H | $CR^6$ | N | 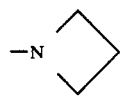 | |
| H | H | H | H | $CR^6$ | N | 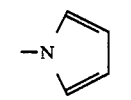 | |
| H | H | H | H | $CR^6$ | N | 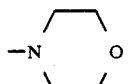 | |
| H | H | H | H | $CR^6$ | N | 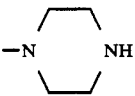 | |
| H | H | H | H | N | $CR^6$ | —$NH_2$ | |
| H | H | H | H | N | $CR^6$ | —NHMe | |
| H | H | H | H | N | $CR^6$ | —NHEt | |
| H | H | H | H | N | $CR^6$ | —NHPh | |
| H | H | H | H | N | $CR^6$ | —NH—$CH_2$Ph | |
| H | H | H | H | N | $CR^6$ | 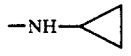 | |
| H | H | H | H | N | $CR^6$ | —NH-i-Pr | |

TABLE-continued (T = SO; A as defined above under (b); R⁴; R⁵ and R⁹ each = hydrogen)

| R¹ | R² | R³ | R⁶ | X | Y | Z | R¹⁰ |
|----|----|----|----|----|----|----|----|
| H | H | H | H | N | CR⁶ | —NH—cyclopentyl 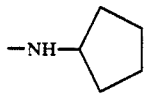 | |
| H | H | H | H | N | CR⁶ | —NH—cyclohexyl 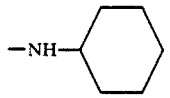 | |
| H | H | H | H | N | CR⁶ | —NMe₂ | |
| H | H | H | H | N | CR⁶ | —NEt₂ | |
| H | H | H | H | N | CR⁶ | —N(iPr)₂ | |
| H | H | H | H | N | CR⁶ | —N(piperidinyl)  | |
| H | H | H | H | N | CR⁶ | —N(pyrrolidinyl)  | |
| H | H | H | H | N | CR⁶ | —N(azetidinyl)  | |
| H | H | H | H | N | CR⁶ | —N(pyrrolyl) 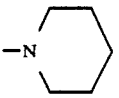 | |
| H | H | H | H | N | CR⁶ | —N(morpholinyl)  | |
| H | H | H | H | N | CR⁶ | —N(piperazinyl)NH 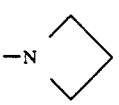 | |
| H | H | H | Cl | CR⁶ | N | —NH₂ | |
| H | H | H | Cl | CR⁶ | N | —NHMe | |
| H | H | H | Cl | CR⁶ | N | —NHEt | |
| H | H | H | Cl | CR⁶ | N | —NHPh | |
| H | H | H | Cl | CR⁶ | N | —NH—CH₂Ph | |
| H | H | H | Cl | CR⁶ | N | —NH—cyclopropyl  | |
| H | H | H | Cl | CR⁶ | N | —NH-i-Pr | |
| H | H | H | Cl | CR⁶ | N | —NH—cyclopentyl 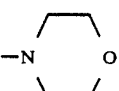 | |
| H | H | H | Cl | CR⁶ | N | —NH—cyclohexyl 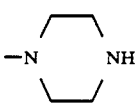 | |
| H | H | H | Cl | CR⁶ | N | —NMe₂ | |
| H | H | H | Cl | CR⁶ | N | —NEt₂ | |
| H | H | H | Cl | CR⁶ | N | —N(iPr)₂ | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | H | Cl | $CR^6$ | N | piperidin-1-yl | |
| H | H | H | Cl | $CR^6$ | N | pyrrolidin-1-yl | |
| H | H | H | Cl | $CR^6$ | N | azetidin-1-yl | |
| H | H | H | Cl | $CR^6$ | N | pyrrol-1-yl | |
| H | H | H | Cl | $CR^6$ | N | morpholin-4-yl | |
| H | H | H | Cl | $CR^6$ | N | piperazin-1-yl | |
| H | H | H | Cl | N | $CR^6$ | $-NH_2$ | |
| H | H | H | Cl | N | $CR^6$ | $-NHMe$ | |
| H | H | H | Cl | N | $CR^6$ | $-NHEt$ | |
| H | H | H | Cl | N | $CR^6$ | $-NHPh$ | |
| H | H | H | Cl | N | $CR^6$ | $-NH-CH_2Ph$ | |
| H | H | H | Cl | N | $CR^6$ | $-NH$-cyclopropyl | |
| H | H | H | Cl | N | $CR^6$ | $-NH$-i-Pr | |
| H | H | H | Cl | N | $CR^6$ | $-NH$-cyclopentyl | |
| H | H | H | Cl | N | $CR^6$ | $-NH$-cyclohexyl | |
| H | H | H | Cl | N | $CR^6$ | $-NMe_2$ | |
| H | H | H | Cl | N | $CR^6$ | $-NEt_2$ | |
| H | H | H | Cl | N | $CR^6$ | $-N(iPr)_2$ | |
| H | H | H | Cl | N | $CR^6$ | piperidin-1-yl | |
| H | H | H | Cl | N | $CR^6$ | pyrrolidin-1-yl | |

TABLE-continued (T = SO; A as defined above under (b); R⁴; R⁵ and R⁹ each = hydrogen)

| R¹ | R² | R³ | R⁶ | X | Y | Z | R¹⁰ |
|----|----|----|----|---|---|---|-----|
| H | H | H | Cl | N | CR⁶ | 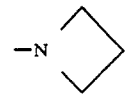 | |
| H | H | H | Cl | N | CR⁶ | 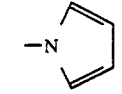 | |
| H | H | H | Cl | N | CR⁶ | 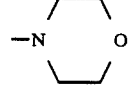 | |
| H | H | H | Cl | N | CR⁶ | 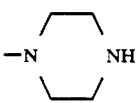 | |
| H | H | H | i-Pr | CR⁶ | N | —NH₂ | |
| H | H | H | i-Pr | CR⁶ | N | —NHMe | |
| H | H | H | i-Pr | CR⁶ | N | —NHEt | |
| H | H | H | i-Pr | CR⁶ | N | —NHPh | |
| H | H | H | i-Pr | CR⁶ | N | —NH—CH₂Ph | |
| H | H | H | i-Pr | CR⁶ | N |  | |
| H | H | H | i-Pr | CR⁶ | N | —NH-i-Pr | |
| H | H | H | i-Pr | CR⁶ | N |  | |
| H | H | H | i-Pr | CR⁶ | N |  | |
| H | H | H | i-Pr | CR⁶ | N | —NMe₂ | |
| H | H | H | i-Pr | CR⁶ | N | —NEt₂ | |
| H | H | H | i-Pr | CR⁶ | N | —N(iPr)₂ | |
| H | H | H | i-Pr | CR⁶ | N |  | |
| H | H | H | i-Pr | CR⁶ | N | 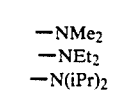 | |
| H | H | H | i-Pr | CR⁶ | N |  | |
| H | H | H | i-Pr | CR⁶ | N | 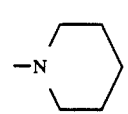 | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | H | i-Pr | $CR^6$ | N | —N(CH₂CH₂)₂O (morpholino) | |
| H | H | H | i-Pr | $CR^6$ | N | —N(CH₂CH₂)₂NH (piperazino) | |
| H | H | H | i-Pr | N | $CR^6$ | —NH₂ | |
| H | H | H | i-Pr | N | $CR^6$ | —NHMe | |
| H | H | H | i-Pr | N | $CR^6$ | —NHEt | |
| H | H | H | i-Pr | N | $CR^6$ | —NHPh | |
| H | H | H | i-Pr | N | $CR^6$ | —NH—CH₂Ph | |
| H | H | H | i-Pr | N | $CR^6$ | —NH-cyclopropyl | |
| H | H | H | i-Pr | N | $CR^6$ | —NH-i-Pr | |
| H | H | H | i-Pr | N | $CR^6$ | —NH-cyclopentyl | |
| H | H | H | i-Pr | N | $CR^6$ | —NH-cyclohexyl | |
| H | H | H | i-Pr | N | $CR^6$ | —NMe₂ | |
| H | H | H | i-Pr | N | $CR^6$ | —NEt₂ | |
| H | H | H | i-Pr | N | $CR^6$ | —N(iPr)₂ | |
| H | H | H | i-Pr | N | $CR^6$ | —N-piperidino | |
| H | H | H | i-Pr | N | $CR^6$ | —N-pyrrolidino | |
| H | H | H | i-Pr | N | $CR^6$ | —N-azetidino | |
| H | H | H | i-Pr | N | $CR^6$ | —N-pyrrolyl | |
| H | H | H | i-Pr | N | $CR^6$ | —N(CH₂CH₂)₂O (morpholino) | |
| H | H | H | i-Pr | N | $CR^6$ | —N(CH₂CH₂)₂NH (piperazino) | |
| H | H | H | Et | N | $CR^6$ | —NH₂ | |
| H | H | H | Et | N | $CR^6$ | —NHMe | |
| H | H | H | Et | N | $CR^6$ | —NHEt | |
| H | H | H | Et | N | $CR^6$ | —NHPh | |

TABLE-continued (T = SO; A as defined above under (b); R⁴; R⁵ and R⁹ each = hydrogen)

| R¹ | R² | R³ | R⁶ | X | Y | Z | R¹⁰ |
|----|----|----|----|----|----|----|----|
| H | H | H | Et | N | CR⁶ | —NH—CH₂Ph | |
| H | H | H | Et | N | CR⁶ | —NH—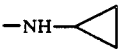 | |
| H | H | H | Et | N | CR⁶ | —NH-i-Pr | |
| H | H | H | Et | N | CR⁶ | —NH—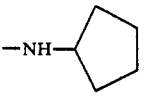 | |
| H | H | H | Et | N | CR⁶ | —NH—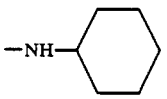 | |
| H | H | H | Et | N | CR⁶ | —NMe₂ | |
| H | H | H | Et | N | CR⁶ | —NEt₂ | |
| H | H | H | Et | N | CR⁶ | —N(iPr)₂ | |
| H | H | H | Et | N | CR⁶ | 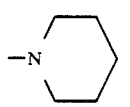 | |
| H | H | H | Et | N | CR⁶ | 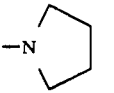 | |
| H | H | H | Et | N | CR⁶ | 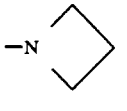 | |
| H | H | H | Et | N | CR⁶ | 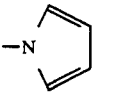 | |
| H | H | H | Et | N | CR⁶ | 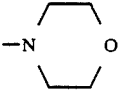 | |
| H | H | H | Et | N | CR⁶ | 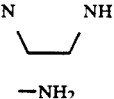 | |
| H | H | H | Et | CR⁶ | N | —NH₂ | |
| H | H | H | Et | CR⁶ | N | —NHMe | |
| H | H | H | Et | CR⁶ | N | —NHEt | |
| H | H | H | Et | CR⁶ | N | —NHPh | |
| H | H | H | Et | CR⁶ | N | —NH—CH₂Ph | |
| H | H | H | Et | CR⁶ | N | —NH—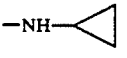 | |
| H | H | H | Et | CR⁶ | N | —NH-i-Pr | |
| H | H | H | Et | CR⁶ | N | —NH—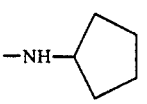 | |

TABLE-continued (T = SO; A as defined above under (b); $R^4$, $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | H | Et | $CR^6$ | N | —NH—cyclohexyl | |
| H | H | H | Et | $CR^6$ | N | —NMe$_2$ | |
| H | H | H | Et | $CR^6$ | N | —NEt$_2$ | |
| H | H | H | Et | $CR^6$ | N | —N(iPr)$_2$ | |
| H | H | H | Et | $CR^6$ | N | —N(piperidinyl) | |
| H | H | H | Et | $CR^6$ | N | —N(pyrrolidinyl) | |
| H | H | H | Et | $CR^6$ | N | —N(azetidinyl) | |
| H | H | H | Et | $CR^6$ | N | —N(pyrrolyl) | |
| H | H | H | Et | $CR^6$ | N | —N(morpholinyl) | |
| H | H | H | Et | $CR^6$ | N | —N(piperazinyl)NH | |
| H | H | H | Me | N | $CR^6$ | —NH$_2$ | |
| H | H | H | Me | N | $CR^6$ | —NHMe | |
| H | H | H | Me | N | $CR^6$ | —NHEt | |
| H | H | H | Me | N | $CR^6$ | —NHPh | |
| H | H | H | Me | N | $CR^6$ | —NH—CH$_2$Ph | |
| H | H | H | Me | N | $CR^6$ | —NH—cyclopropyl | |
| H | H | H | Me | N | $CR^6$ | —NH-i-Pr | |
| H | H | H | Me | N | $CR^6$ | —NH—cyclopentyl | |
| H | H | H | Me | N | $CR^6$ | —NH—cyclohexyl | |
| H | H | H | Me | N | $CR^6$ | —NMe$_2$ | |
| H | H | H | Me | N | $CR^6$ | —NEt$_2$ | |
| H | H | H | Me | N | $CR^6$ | —N(iPr)$_2$ | |
| H | H | H | Me | N | $CR^6$ | —N(piperidinyl) | |

TABLE-continued
(T = SO; A as defined above under (b); R⁴; R⁵ and R⁹ each = hydrogen)
| R¹ | R² | R³ | R⁶ | X | Y | Z | R¹⁰ |
|----|----|----|----|----|----|---|-----|
| H | H | H | Me | N | CR⁶ |  | |
| H | H | H | Me | N | CR⁶ | 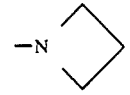 | |
| H | H | H | Me | N | CR⁶ |  | |
| H | H | H | Me | N | CR⁶ | 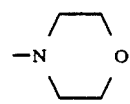 | |
| H | H | H | Me | N | CR⁶ | 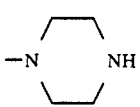 | |
| H | H | H | Me | CR⁶ | N | —NH₂ | |
| H | H | H | Me | CR⁶ | N | —NHMe | |
| H | H | H | Me | CR⁶ | N | —NHEt | |
| H | H | H | Me | CR⁶ | N | —NHPh | |
| H | H | H | Me | CR⁶ | N | —NH—CH₂Ph | |
| H | H | H | Me | CR⁶ | N |  | |
| H | H | H | Me | CR⁶ | N | —NH-i-Pr | |
| H | H | H | Me | CR⁶ | N |  | |
| H | H | H | Me | CR⁶ | N |  | |
| H | H | H | Me | CR⁶ | N | —NMe₂ | |
| H | H | H | Me | CR⁶ | N | —NEt₂ | |
| H | H | H | Me | CR⁶ | N | —N(iPr)₂ | |
| H | H | H | Me | CR⁶ | N |  | |
| H | H | H | Me | CR⁶ | N |  | |
| H | H | H | Me | CR⁶ | N | 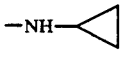 | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | H | Me | $CR^6$ | N |  | |
| H | H | H | Me | $CR^6$ | N | 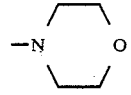 | |
| H | H | H | Me | $CR^6$ | N |  | |
| Cl | H | H | Et | N | $CR^6$ | —NH$_2$ | |
| Cl | H | H | Et | N | $CR^6$ | —NHMe | |
| Cl | H | H | Et | N | $CR^6$ | —NHEt | |
| H | H | H | Et | N | $CR^6$ | —NHPh | |
| Cl | H | H | Et | N | $CR^6$ | —NH—CH$_2$Ph | |
| Cl | H | H | Et | N | $CR^6$ | 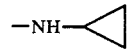 | |
| Cl | H | H | Et | N | $CR^6$ | —NH-i-Pr | |
| Cl | H | H | Et | N | $CR^6$ | 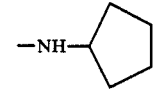 | |
| Cl | H | H | Et | N | $CR^6$ | 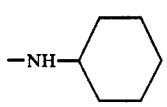 | |
| Cl | H | H | Et | N | $CR^6$ | —NMe$_2$ | |
| Cl | H | H | Et | N | $CR^6$ | —NEt$_2$ | |
| Cl | H | H | Et | N | $CR^6$ | —N(iPr)$_2$ | |
| Cl | H | H | Et | N | $CR^6$ | 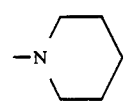 | |
| Cl | H | H | Et | N | $CR^6$ | 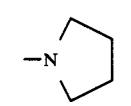 | |
| Cl | H | H | Et | N | $CR^6$ | 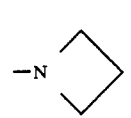 | |
| Cl | H | H | Et | N | $CR^6$ |  | |
| Cl | H | H | Et | N | $CR^6$ | 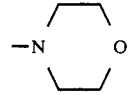 | |

TABLE-continued

| | | | (T = SO; A as defined above under (b); R⁴; R⁵ and R⁹ each = hydrogen) | | | | |
|---|---|---|---|---|---|---|---|
| $R^1$ | $R^2$ | $R^3$ | $R^6$ | X | Y | Z | $R^{10}$ |
| Cl | H | H | Et | N | $CR^6$ |  | |
| Cl | H | H | Et | $CR^6$ | N | —NH₂ | |
| Cl | H | H | Et | $CR^6$ | N | —NHMe | |
| Cl | H | H | Et | $CR^6$ | N | —NHEt | |
| Cl | H | H | Et | $CR^6$ | N | —NHPh | |
| Cl | H | H | Et | $CR^6$ | N | —NH—CH₂Ph | |
| Cl | H | H | Et | $CR^6$ | N | 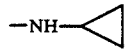 | |
| Cl | H | H | Et | $CR^6$ | N | —NH-i-Pr | |
| Cl | H | H | Et | $CR^6$ | N | 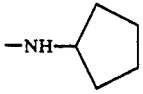 | |
| Cl | H | H | Et | $CR^6$ | N | 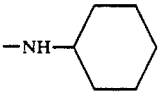 | |
| Cl | H | H | Et | $CR^6$ | N | —NMe₂ | |
| Cl | H | H | Et | $CR^6$ | N | —NEt₂ | |
| Cl | H | H | Et | $CR^6$ | N | —N(iPr)₂ | |
| Cl | H | H | Et | $CR^6$ | N | 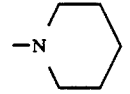 | |
| Cl | H | H | Et | $CR^6$ | N | 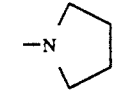 | |
| Cl | H | H | Et | $CR^6$ | N | 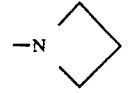 | |
| Cl | H | H | Et | $CR^6$ | N | 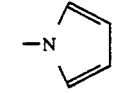 | |
| Cl | H | H | Et | $CR^6$ | N | 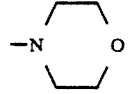 | |
| Cl | H | H | Et | $CR^6$ | N |  | |
| Cl | H | H | Me | N | $CR^6$ | —NH₂ | |
| Cl | H | H | Me | N | $CR^6$ | —NHMe | |
| Cl | H | H | Me | N | $CR^6$ | —NHEt | |
| Cl | H | H | Me | N | $CR^6$ | —NHPh | |
| Cl | H | H | Me | N | $CR^6$ | —NH—CH₂Ph | |
| Cl | H | H | Me | N | $CR^6$ | 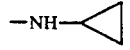 | |

TABLE-continued (T = SO; A as defined above under (b); R⁴; R⁵ and R⁹ each = hydrogen)

| $R^1$ | $R^2$ | $R^3$ | $R^6$ | X | Y | Z | $R^{10}$ |
|---|---|---|---|---|---|---|---|
| Cl | H | H | Me | N | $CR^6$ | —NH-i-Pr | |
| Cl | H | H | Me | N | $CR^6$ | —NH-cyclopentyl | |
| Cl | H | H | Me | N | $CR^6$ | —NH-cyclohexyl | |
| Cl | H | H | Me | N | $CR^6$ | —NMe₂ | |
| Cl | H | H | Me | N | $CR^6$ | —NEt₂ | |
| Cl | H | H | Me | N | $CR^6$ | —N(iPr)₂ | |
| Cl | H | H | Me | N | $CR^6$ | —N-piperidinyl | |
| Cl | H | H | Me | N | $CR^6$ | —N-pyrrolidinyl | |
| Cl | H | H | Me | N | $CR^6$ | —N-azetidinyl | |
| Cl | H | H | Me | N | $CR^6$ | —N-pyrrolyl | |
| Cl | H | H | Me | N | $CR^6$ | —N-morpholinyl | |
| Cl | H | H | Me | N | $CR^6$ | —N-piperazinyl | |
| Cl | H | H | Me | $CR^6$ | N | —NH₂ | |
| Cl | H | H | Me | $CR^6$ | N | —NHMe | |
| Cl | H | H | Me | $CR^6$ | N | —NHEt | |
| Cl | H | H | Me | $CR^6$ | N | —NHPh | |
| Cl | H | H | Me | $CR^6$ | N | —NH—CH₂Ph | |
| Cl | H | H | Me | $CR^6$ | N | —NH-cyclopropyl | |
| Cl | H | H | Me | $CR^6$ | N | —NH-i-Pr | |
| Cl | H | H | Me | $CR^6$ | N | —NH-cyclopentyl | |
| Cl | H | H | Me | $CR^6$ | N | —NH-cyclohexyl | |
| Cl | H | H | Me | $CR^6$ | N | —NMe₂ | |
| Cl | H | H | Me | $CR^6$ | N | —NEt₂ | |

TABLE-continued (T = SO; A as defined above under (b); R⁴; R⁵ and R⁹ each = hydrogen)

| R¹ | R² | R³ | R⁶ | X | Y | Z | R¹⁰ |
|----|----|----|----|---|---|---|-----|
| Cl | H | H | Me | CR⁶ | N | —N(iPr)₂ | |
| Cl | H | H | Me | CR⁶ | N | 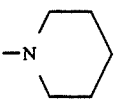 | |
| Cl | H | H | Me | CR⁶ | N | 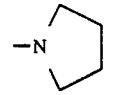 | |
| Cl | H | H | Me | CR⁶ | N |  | |
| Cl | H | H | Me | CR⁶ | N | 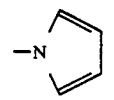 | |
| Cl | H | H | Me | CR⁶ | N | 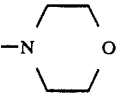 | |
| Cl | H | H | Me | CR⁶ | N | 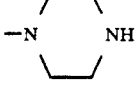 | |
| H | H | CO₂t-Bu | i-Pr | CR⁶ | N | —NH₂ | |
| H | H | CO₂t-Bu | i-Pr | CR⁶ | N | —NHMe | |
| H | H | CO₂t-Bu | i-Pr | CR⁶ | N | —NHEt | |
| H | H | CO₂t-Bu | i-Pr | CR⁶ | N | —NHPh | |
| H | H | CO₂t-Bu | i-Pr | CR⁶ | N | —NH—CH₂Ph | |
| H | H | CO₂t-Bu | i-Pr | CR⁶ | N | 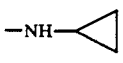 | |
| H | H | CO₂t-Bu | i-Pr | CR⁶ | N | —NH-i-Pr | |
| H | H | CO₂t-Bu | i-Pr | CR⁶ | N | 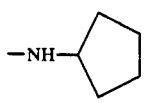 | |
| H | H | CO₂t-Bu | i-Pr | CR⁶ | N | 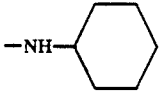 | |
| H | H | CO₂t-Bu | i-Pr | CR⁶ | N | —NMe₂ | |
| H | H | CO₂t-Bu | i-Pr | CR⁶ | N | —NEt₂ | |
| H | H | CO₂t-Bu | i-Pr | CR⁶ | N | —N(iPr)₂ | |
| H | H | CO₂t-Bu | i-Pr | CR⁶ | N | 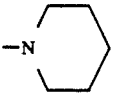 | |
| H | H | CO₂t-Bu | i-Pr | CR⁶ | N | 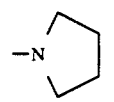 | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | $CO_2$t-Bu | i-Pr | $CR^6$ | N | 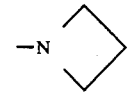 | |
| H | H | $CO_2$t-Bu | i-Pr | $CR^6$ | N | 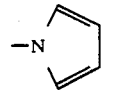 | |
| H | H | $CO_2$t-Bu | i-Pr | $CR^6$ | N | 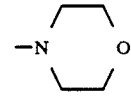 | |
| H | H | $CO_2$t-Bu | i-Pr | $CR^6$ | N | 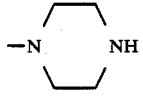 | |
| H | H | $CO_2$t-Bu | i-Pr | N | $CR^6$ | —$NH_2$ | |
| H | H | $CO_2$t-Bu | i-Pr | N | $CR^6$ | —NHMe | |
| H | H | $CO_2$t-Bu | i-Pr | N | $CR^6$ | —NHEt | |
| H | H | $CO_2$t-Bu | i-Pr | N | $CR^6$ | —NHPh | |
| H | H | $CO_2$t-Bu | i-Pr | N | $CR^6$ | —NH—$CH_2$Ph | |
| H | H | $CO_2$t-Bu | i-Pr | N | $CR^6$ |  | |
| H | H | $CO_2$t-Bu | i-Pr | N | $CR^6$ | —NH-i-Pr | |
| H | H | $CO_2$t-Bu | i-Pr | N | $CR^6$ |  | |
| H | H | $CO_2$t-Bu | i-Pr | N | $CR^6$ |  | |
| H | H | $CO_2$t-Bu | i-Pr | N | $CR^6$ | —$NMe_2$ | |
| H | H | $CO_2$t-Bu | i-Pr | N | $CR^6$ | —$NEt_2$ | |
| H | H | $CO_2$t-Bu | i-Pr | N | $CR^6$ | —$N(iPr)_2$ | |
| H | H | $CO_2$t-Bu | i-Pr | N | $CR^6$ |  | |
| H | H | $CO_2$t-Bu | i-Pr | N | $CR^6$ |  | |
| H | H | $CO_2$t-Bu | i-Pr | N | $CR^6$ | 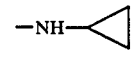 | |
| H | H | $CO_2$t-Bu | i-Pr | N | $CR^6$ |  | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | $CO_2$t-Bu | i-Pr | N | $CR^6$ | —N⟨morpholino⟩ | |
| H | H | $CO_2$t-Bu | i-Pr | N | $CR^6$ | —N⟨piperazinyl-NH⟩ | |
| H | H | $CO_2$t-Bu | Et | N | $CR^6$ | —$NH_2$ | |
| H | H | $CO_2$t-Bu | Et | N | $CR^6$ | —NHMe | |
| H | H | $CO_2$t-Bu | Et | N | $CR^6$ | —NHEt | |
| H | H | $CO_2$t-Bu | Et | N | $CR^6$ | —NHPh | |
| H | H | $CO_2$t-Bu | Et | N | $CR^6$ | —NH—$CH_2$Ph | |
| H | H | $CO_2$t-Bu | Et | N | $CR^6$ | —NH—cyclopropyl | |
| H | H | $CO_2$t-Bu | Et | N | $CR^6$ | —NH-i-Pr | |
| H | H | $CO_2$t-Bu | Et | N | $CR^6$ | —NH—cyclopentyl | |
| H | H | $CO_2$t-Bu | Et | N | $CR^6$ | —NH—cyclohexyl | |
| H | H | $CO_2$t-Bu | Et | N | $CR^6$ | —$NMe_2$ | |
| H | H | $CO_2$t-Bu | Et | N | $CR^6$ | —$NEt_2$ | |
| H | H | $CO_2$t-Bu | Et | N | $CR^6$ | —$N(iPr)_2$ | |
| H | H | $CO_2$t-Bu | Et | N | $CR^6$ | —N⟨piperidinyl⟩ | |
| H | H | $CO_2$t-Bu | Et | N | $CR^6$ | —N⟨pyrrolidinyl⟩ | |
| H | H | $CO_2$t-Bu | Et | N | $CR^6$ | —N⟨azetidinyl⟩ | |
| H | H | $CO_2$t-Bu | Et | N | $CR^6$ | —N⟨pyrrolyl⟩ | |
| H | H | $CO_2$t-Bu | Et | N | $CR^6$ | —N⟨morpholino⟩ | |
| H | H | $CO_2$t-Bu | Et | N | $CR^6$ | —N⟨piperazinyl-NH⟩ | |
| H | H | $CO_2$t-Bu | Et | $CR^6$ | N | —$NH_2$ | |
| H | H | $CO_2$t-Bu | Et | $CR^6$ | N | —NHMe | |
| H | H | $CO_2$t-Bu | Et | $CR^6$ | N | —NHEt | |
| H | H | $CO_2$t-Bu | Et | $CR^6$ | N | —NHPh | |

TABLE-continued (T = SO; A as defined above under (b); R⁴; R⁵ and R⁹ each = hydrogen)

| R$^1$ | R$^2$ | R$^3$ | R$^6$ | X | Y | Z | R$^{10}$ |
|---|---|---|---|---|---|---|---|
| H | H | CO$_2$t-Bu | Et | CR$^6$ | N | —NH—CH$_2$Ph | |
| H | H | CO$_2$t-Bu | Et | CR$^6$ | N | —NH—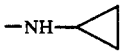 | |
| H | H | CO$_2$t-Bu | Et | CR$^6$ | N | —NH-i-Pr | |
| H | H | CO$_2$t-Bu | Et | CR$^6$ | N | —NH—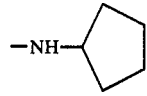 | |
| H | H | CO$_2$t-Bu | Et | CR$^6$ | N | —NH—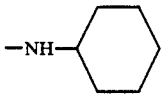 | |
| H | H | CO$_2$t-Bu | Et | CR$^6$ | N | —NMe$_2$ | |
| H | H | CO$_2$t-Bu | Et | CR$^6$ | N | —NEt$_2$ | |
| H | H | CO$_2$t-Bu | Et | CR$^6$ | N | —N(iPr)$_2$ | |
| H | H | CO$_2$t-Bu | Et | CR$^6$ | N | 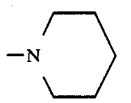 | |
| H | H | CO$_2$t-Bu | Et | CR$^6$ | N |  | |
| H | H | CO$_2$t-Bu | Et | CR$^6$ | N | 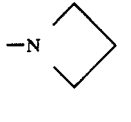 | |
| H | H | CO$_2$t-Bu | Et | CR$^6$ | N |  | |
| H | H | CO$_2$t-Bu | Et | CR$^6$ | N | 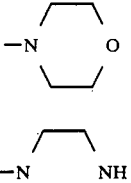 | |
| H | H | CO$_2$t-Bu | Et | CR$^6$ | N | 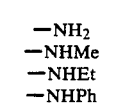 | |
| H | H | CO$_2$t-Bu | NH$_2$ | N | CR$^6$ | —NH$_2$ | |
| H | H | CO$_2$t-Bu | NH$_2$ | N | CR$^6$ | —NHMe | |
| H | H | CO$_2$t-Bu | NH$_2$ | N | CR$^6$ | —NHEt | |
| H | H | CO$_2$t-Bu | NH$_2$ | N | CR$^6$ | —NHPh | |
| H | H | CO$_2$t-Bu | NH$_2$ | N | CR$^6$ | —NH—CH$_2$Ph | |
| H | H | CO$_2$t-Bu | NH$_2$ | N | CR$^6$ | —NH— | |
| H | H | CO$_2$t-Bu | NH$_2$ | N | CR$^6$ | —NH-i-Pr | |
| H | H | CO$_2$t-Bu | NH$_2$ | N | CR$^6$ | —NH—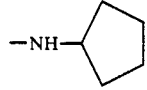 | |

TABLE-continued (T = SO; A as defined above under (b); R⁴; R⁵ and R⁹ each = hydrogen)

| $R^1$ | $R^2$ | $R^3$ | $R^6$ | X | Y | Z | $R^{10}$ |
|---|---|---|---|---|---|---|---|
| H | H | CO₂t-Bu | NH₂ | N | CR⁶ | —NH—cyclohexyl | |
| H | H | CO₂t-Bu | NH₂ | N | CR⁶ | —NMe₂ | |
| H | H | CO₂t-Bu | NH₂ | N | CR⁶ | —NEt₂ | |
| H | H | CO₂t-Bu | NH₂ | N | CR⁶ | —N(iPr)₂ | |
| H | H | CO₂t-Bu | NH₂ | N | CR⁶ | —N(piperidinyl) | |
| H | H | CO₂t-Bu | NH₂ | N | CR⁶ | —N(pyrrolidinyl) | |
| H | H | CO₂t-Bu | NH₂ | N | CR⁶ | —N(azetidinyl) | |
| H | H | CO₂t-Bu | NH₂ | N | CR⁶ | —N(pyrrolyl) | |
| H | H | CO₂t-Bu | NH₂ | N | CR⁶ | —N(morpholinyl) | |
| H | H | CO₂t-Bu | NH₂ | N | CR⁶ | —N(piperazinyl)NH | |
| H | H | CO₂t-Bu | Me | N | CR⁶ | —NH₂ | |
| H | H | CO₂t-Bu | Me | N | CR⁶ | —NHMe | |
| H | H | CO₂t-Bu | Me | N | CR⁶ | —NHEt | |
| H | H | CO₂t-Bu | Me | N | CR⁶ | —NHPh | |
| H | H | CO₂t-Bu | Me | N | CR⁶ | —NH—CH₂Ph | |
| H | H | CO₂t-Bu | Me | N | CR⁶ | —NH—cyclopropyl | |
| H | H | CO₂t-Bu | Me | N | CR⁶ | —NH-i-Pr | |
| H | H | CO₂t-Bu | Me | N | CR⁶ | —NH—cyclopentyl | |
| H | H | CO₂t-Bu | Me | N | CR⁶ | —NH—cyclohexyl | |
| H | H | CO₂t-Bu | Me | N | CR⁶ | —NMe₂ | |
| H | H | CO₂t-Bu | Me | N | CR⁶ | —NEt₂ | |
| H | H | CO₂t-Bu | Me | N | CR⁶ | —N(iPr)₂ | |
| H | H | CO₂t-Bu | Me | N | CR⁶ | —N(piperidinyl) | |

TABLE-continued

| | | (T = SO; A as defined above under (b); R⁴; R⁵ and R⁹ each = hydrogen) | | | | | |
|---|---|---|---|---|---|---|---|
| $R^1$ | $R^2$ | $R^3$ | $R^6$ | X | Y | Z | $R^{10}$ |
| H | H | $CO_2t$-Bu | Me | N | $CR^6$ | 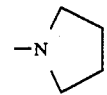 | |
| H | H | $CO_2t$-Bu | Me | N | $CR^6$ | 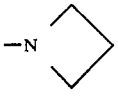 | |
| H | H | $CO_2t$-Bu | Me | N | $CR^6$ | 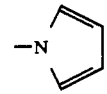 | |
| H | H | $CO_2t$-Bu | Me | N | $CR^6$ | 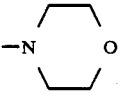 | |
| H | H | $CO_2t$-Bu | Me | N | $CR^6$ | 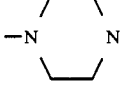 | |
| H | H | $CO_2t$-Bu | Me | $CR^6$ | N | —NH₂ | |
| H | H | $CO_2t$-Bu | Me | $CR^6$ | N | —NHMe | |
| H | H | $CO_2t$-Bu | Me | $CR^6$ | N | —NHEt | |
| H | H | $CO_2t$-Bu | Me | $CR^6$ | N | —NHPh | |
| H | H | $CO_2t$-Bu | Me | $CR^6$ | N | —NH—CH₂Ph | |
| H | H | $CO_2t$-Bu | Me | $CR^6$ | N | 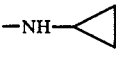 | |
| H | H | $CO_2t$-Bu | Me | $CR^6$ | N | —NH-i-Pr | |
| H | H | $CO_2t$-Bu | Me | $CR^6$ | N |  | |
| H | H | $CO_2t$-Bu | Me | $CR^6$ | N | 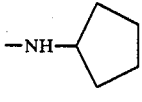 | |
| H | H | $CO_2t$-Bu | Me | $CR^6$ | N | —NMe₂ | |
| H | H | $CO_2t$-Bu | Me | $CR^6$ | N | —NEt₂ | |
| H | H | $CO_2t$-Bu | Me | $CR^6$ | N | —N(iPr)₂ | |
| H | H | $CO_2t$-Bu | Me | $CR^6$ | N | 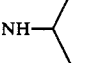 | |
| H | H | $CO_2t$-Bu | Me | $CR^6$ | N | 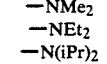 | |
| H | H | $CO_2t$-Bu | Me | $CR^6$ | N | 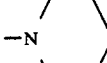 | |

TABLE-continued

| | | (T = SO; A as defined above under (b); $R^4$; $R^5$ and $R^9$ each = hydrogen) | | | | | |
|---|---|---|---|---|---|---|---|
| $R^1$ | $R^2$ | $R^3$ | $R^6$ | X | Y | Z | $R^{10}$ |
| H | H | $CO_2$t-Bu | Me | $CR^6$ | N |  | |
| H | H | $CO_2$t-Bu | Me | $CR^6$ | N |  | |
| H | H | $CO_2$t-Bu | Me | $CR^6$ | N |  | |
| H | H | H | $NH_2$ | $CR^6$ | N | $-NH_2$ | |
| H | H | H | $NH_2$ | $CR^6$ | N | $-NHMe$ | |
| H | H | H | $NH_2$ | $CR^6$ | N | $-NHEt$ | |
| H | H | H | $NH_2$ | $CR^6$ | N | $-NHPh$ | |
| H | H | H | $NH_2$ | $CR^6$ | N | $-NH-CH_2Ph$ | |
| H | H | H | $NH_2$ | $CR^6$ | N |  | |
| H | H | H | $NH_2$ | $CR^6$ | N | $-NH$-i-Pr | |
| H | H | H | $NH_2$ | $CR^6$ | N |  | |
| H | H | H | $NH_2$ | $CR^6$ | N |  | |
| H | H | H | $NH_2$ | $CR^6$ | N | $-NMe_2$ | |
| H | H | H | $NH_2$ | $CR^6$ | N | $-NEt_2$ | |
| H | H | H | $NH_2$ | $CR^6$ | N | $-N(iPr)_2$ | |
| H | H | H | $NH_2$ | $CR^6$ | N |  | |
| H | H | H | $NH_2$ | $CR^6$ | N |  | |
| H | H | H | $NH_2$ | $CR^6$ | N |  | |
| H | H | H | $NH_2$ | $CR^6$ | N |  | |
| H | H | H | $NH_2$ | $CR^6$ | N | 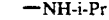 | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | H | $NH_2$ | $CR^6$ | N | −N⟨piperazine⟩NH | |
| H | H | H | $NH_2$ | N | $CR^6$ | $−NH_2$ | |
| H | H | H | $NH_2$ | N | $CR^6$ | −NHMe | |
| H | H | H | $NH_2$ | N | $CR^6$ | −NHEt | |
| H | H | H | $NH_2$ | N | $CR^6$ | −NHPh | |
| H | H | H | $NH_2$ | N | $CR^6$ | −NH−$CH_2$Ph | |
| H | H | H | $NH_2$ | N | $CR^6$ | −NH−cyclopropyl | |
| H | H | H | $NH_2$ | N | $CR^6$ | −NH-i-Pr | |
| H | H | H | $NH_2$ | N | $CR^6$ | −NH−cyclopentyl | |
| H | H | H | $NH_2$ | N | $CR^6$ | −NH−cyclohexyl | |
| H | H | H | $NH_2$ | N | $CR^6$ | $−NMe_2$ | |
| H | H | H | $NH_2$ | N | $CR^6$ | $−NEt_2$ | |
| H | H | H | $NH_2$ | N | $CR^6$ | $−N(iPr)_2$ | |
| H | H | H | $NH_2$ | N | $CR^6$ | −N⟨piperidine⟩ | |
| H | H | H | $NH_2$ | N | $CR^6$ | −N⟨pyrrolidine⟩ | |
| H | H | H | $NH_2$ | N | $CR^6$ | −N⟨azetidine⟩ | |
| H | H | H | $NH_2$ | N | $CR^6$ | −N⟨pyrrole⟩ | |
| H | H | H | $NH_2$ | N | $CR^6$ | −N⟨morpholine⟩O | |
| H | H | H | $NH_2$ | N | $CR^6$ | −N⟨piperazine⟩NH | |
| H | H | $CO_2$t-Bu | $NH_2$ | $CR^6$ | N | $−NH_2$ | |
| H | H | $CO_2$t-Bu | $NH_2$ | $CR^6$ | N | −NHMe | |
| H | H | $CO_2$t-Bu | $NH_2$ | $CR^6$ | N | −NHEt | |
| H | H | $CO_2$t-Bu | $NH_2$ | $CR^6$ | N | −NHPh | |
| H | H | $CO_2$t-Bu | $NH_2$ | $CR^6$ | N | −NH−$CH_2$Ph | |
| H | H | $CO_2$t-Bu | $NH_2$ | $CR^6$ | N | −NH−cyclopropyl | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | $CO_2$t-Bu | $NH_2$ | $CR^6$ | N | —NH-i-Pr | |
| H | H | $CO_2$t-Bu | $NH_2$ | $CR^6$ | N | 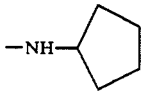 | |
| H | H | $CO_2$t-Bu | $NH_2$ | $CR^6$ | N | 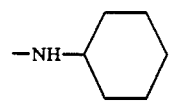 | |
| H | H | $CO_2$t-Bu | $NH_2$ | $CR^6$ | N | —$NMe_2$ | |
| H | H | $CO_2$t-Bu | $NH_2$ | $CR^6$ | N | —$NEt_2$ | |
| H | H | $CO_2$t-Bu | $NH_2$ | $CR^6$ | N | —$N(iPr)_2$ | |
| H | H | $CO_2$t-Bu | $NH_2$ | $CR^6$ | N | 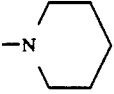 | |
| H | H | $CO_2$t-Bu | $NH_2$ | $CR^6$ | N |  | |
| H | H | $CO_2$t-Bu | $NH_2$ | $CR^6$ | N | 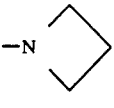 | |
| H | H | $CO_2$t-Bu | $NH_2$ | $CR^6$ | N | 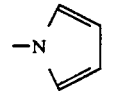 | |
| H | H | $CO_2$t-Bu | $NH_2$ | $CR^6$ | N | 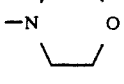 | |
| H | H | $CO_2$t-Bu | $NH_2$ | $CR^6$ | N | 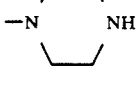 | |
| Cl | H | H | Cl | $CR^6$ | N | —$NH_2$ | |
| Cl | H | H | Cl | $CR^6$ | N | —NHMe | |
| Cl | H | H | Cl | $CR^6$ | N | —NHEt | |
| Cl | H | H | Cl | $CR^6$ | N | —NHPh | |
| Cl | H | H | Cl | $CR^6$ | N | —NH—$CH_2$Ph | |
| Cl | H | H | Cl | $CR^6$ | N | 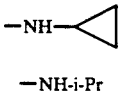 | |
| Cl | H | H | Cl | $CR^6$ | N | —NH-i-Pr | |
| Cl | H | H | Cl | $CR^6$ | N | 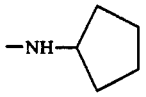 | |
| Cl | H | H | Cl | $CR^6$ | N | 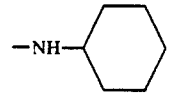 | |
| Cl | H | H | Cl | $CR^6$ | N | —$NMe_2$ | |
| Cl | H | H | Cl | $CR^6$ | N | —$NEt_2$ | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| Cl | H | H | Cl | $CR^6$ | N | —N(iPr)$_2$ | |
| Cl | H | H | Cl | $CR^6$ | N | —N(piperidinyl) | |
| Cl | H | H | Cl | $CR^6$ | N | —N(pyrrolidinyl) | |
| Cl | H | H | Cl | $CR^6$ | N | —N(azetidinyl) | |
| Cl | H | H | Cl | $CR^6$ | N | —N(pyrrolyl) | |
| Cl | H | H | Cl | $CR^6$ | N | —N(morpholinyl) | |
| Cl | H | H | Cl | $CR^6$ | N | —N(piperazinyl)NH | |
| Cl | H | H | Cl | N | $CR^6$ | —NH$_2$ | |
| Cl | H | H | Cl | N | $CR^6$ | —NHMe | |
| Cl | H | H | Cl | N | $CR^6$ | —NHEt | |
| Cl | H | H | Cl | N | $CR^6$ | —NHPh | |
| Cl | H | H | Cl | N | $CR^6$ | —NH—CH$_2$Ph | |
| Cl | H | H | Cl | N | $CR^6$ | —NH-cyclopropyl | |
| Cl | H | H | Cl | N | $CR^6$ | —NH-i-Pr | |
| Cl | H | H | Cl | N | $CR^6$ | —NH-cyclopentyl | |
| Cl | H | H | Cl | N | $CR^6$ | —NH-cyclohexyl | |
| Cl | H | H | Cl | N | $CR^6$ | —NMe$_2$ | |
| Cl | H | H | Cl | N | $CR^6$ | —NEt$_2$ | |
| Cl | H | H | Cl | N | $CR^6$ | —N(iPr)$_2$ | |
| Cl | H | H | Cl | N | $CR^6$ | —N(piperidinyl) | |
| Cl | H | H | Cl | N | $CR^6$ | —N(pyrrolidinyl) | |

TABLE-continued

| (T = SO; A as defined above under (b); $R^4$; $R^5$ and $R^9$ each = hydrogen) | | | | | | | |
|---|---|---|---|---|---|---|---|
| $R^1$ | $R^2$ | $R^3$ | $R^6$ | X | Y | Z | $R^{10}$ |
| Cl | H | H | Cl | N | $CR^6$ | 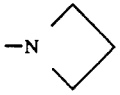 | |
| Cl | H | H | Cl | N | $CR^6$ |  | |
| Cl | H | H | Cl | N | $CR^6$ | 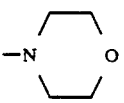 | |
| Cl | H | H | Cl | N | $CR^6$ |  | |
| Cl | H | H | i-Pr | N | $CR^6$ | —NH$_2$ | |
| Cl | H | H | i-Pr | N | $CR^6$ | —NHMe | |
| Cl | H | H | i-Pr | N | $CR^6$ | —NHEt | |
| Cl | H | H | i-Pr | N | $CR^6$ | —NHPh | |
| Cl | H | H | i-Pr | N | $CR^6$ | —NH—CH$_2$Ph | |
| Cl | H | H | i-Pr | N | $CR^6$ | 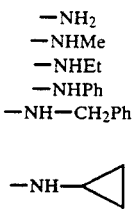 | |
| Cl | H | H | i-Pr | N | $CR^6$ | —NH-i-Pr | |
| Cl | H | H | i-Pr | N | $CR^6$ | 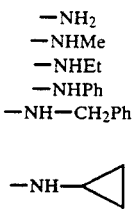 | |
| Cl | H | H | i-Pr | N | $CR^6$ | 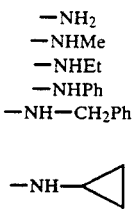 | |
| Cl | H | H | i-Pr | N | $CR^6$ | —NMe$_2$ | |
| Cl | H | H | i-Pr | N | $CR^6$ | —NEt$_2$ | |
| Cl | H | H | i-Pr | N | $CR^6$ | —N(iPr)$_2$ | |
| Cl | H | H | i-Pr | N | $CR^6$ | 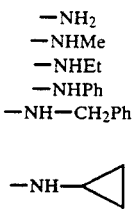 | |
| Cl | H | H | i-Pr | N | $CR^6$ | 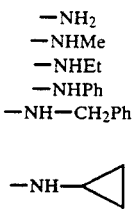 | |
| Cl | H | H | i-Pr | N | $CR^6$ | 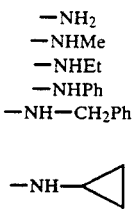 | |
| Cl | H | H | i-Pr | N | $CR^6$ | 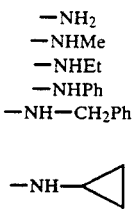 | |

TABLE-continued

| | | | (T = SO; A as defined above under (b); R⁴; R⁵ and R⁹ each = hydrogen) | | | | |
|---|---|---|---|---|---|---|---|
| R¹ | R² | R³ | R⁶ | X | Y | Z | R¹⁰ |
| Cl | H | H | i-Pr | N | CR⁶ | —N(morpholine, O) | |
| Cl | H | H | i-Pr | N | CR⁶ | —N(piperazine, NH) | |
| Cl | H | H | i-Pr | CR⁶ | N | —NH₂ | |
| Cl | H | H | i-Pr | CR⁶ | N | —NHMe | |
| Cl | H | H | i-Pr | CR⁶ | N | —NHEt | |
| Cl | H | H | i-Pr | CR⁶ | N | —NHPh | |
| Cl | H | H | i-Pr | CR⁶ | N | —NH—CH₂Ph | |
| Cl | H | H | i-Pr | CR⁶ | N | —NH-cyclopropyl | |
| Cl | H | H | i-Pr | CR⁶ | N | —NH-i-Pr | |
| Cl | H | H | i-Pr | CR⁶ | N | —NH-cyclopentyl | |
| Cl | H | H | i-Pr | CR⁶ | N | —NH-cyclohexyl | |
| Cl | H | H | i-Pr | CR⁶ | N | —NMe₂ | |
| Cl | H | H | i-Pr | CR⁶ | N | —NEt₂ | |
| Cl | H | H | i-Pr | CR⁶ | N | —N(iPr)₂ | |
| Cl | H | H | i-Pr | CR⁶ | N | —N(piperidine) | |
| Cl | H | H | i-Pr | CR⁶ | N | —N(pyrrolidine) | |
| Cl | H | H | i-Pr | CR⁶ | N | —N(azetidine) | |
| Cl | H | H | i-Pr | CR⁶ | N | —N(pyrrole) | |
| Cl | H | H | i-Pr | CR⁶ | N | —N(morpholine, O) | |
| Cl | H | H | i-Pr | CR⁶ | N | —N(piperazine, NH) | |
| H | H | CO₂t-Bu | | Cl | N | CR⁶ | —NH₂ |
| H | H | CO₂t-Bu | | Cl | N | CR⁶ | —NHMe |
| H | H | CO₂t-Bu | | Cl | N | CR⁶ | —NHEt |
| H | H | CO₂t-Bu | | Cl | N | CR⁶ | —NHPh |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | CO$_2$t-Bu | Cl | N | CR$^6$ | —NH—CH$_2$Ph | |
| H | H | CO$_2$t-Bu | Cl | N | CR$^6$ | —NH—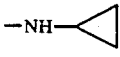 | |
| H | H | CO$_2$t-Bu | Cl | N | CR$^6$ | —NH-i-Pr | |
| H | H | CO$_2$t-Bu | Cl | N | CR$^6$ | —NH—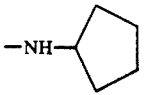 | |
| H | H | CO$_2$t-Bu | Cl | N | CR$^6$ | —NH—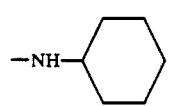 | |
| H | H | CO$_2$t-Bu | Cl | N | CR$^6$ | —NMe$_2$ | |
| H | H | CO$_2$t-Bu | Cl | N | CR$^6$ | —NEt$_2$ | |
| H | H | CO$_2$t-Bu | Cl | N | CR$^6$ | —N(iPr)$_2$ | |
| H | H | CO$_2$t-Bu | Cl | N | CR$^6$ | 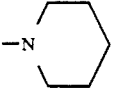 | |
| H | H | CO$_2$t-Bu | Cl | N | CR$^6$ |  | |
| H | H | CO$_2$t-Bu | Cl | N | CR$^6$ | 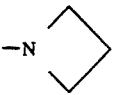 | |
| H | H | CO$_2$t-Bu | Cl | N | CR$^6$ | 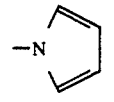 | |
| H | H | CO$_2$t-Bu | Cl | N | CR$^6$ |  | |
| H | H | CO$_2$t-Bu | Cl | N | CR$^6$ |  | |
| H | H | CO$_2$t-Bu | Cl | CR$^6$ | N | —NH$_2$ | |
| H | H | CO$_2$t-Bu | Cl | CR$^6$ | N | —NHMe | |
| H | H | CO$_2$t-Bu | Cl | CR$^6$ | N | —NHEt | |
| H | H | CO$_2$t-Bu | Cl | CR$^6$ | N | —NHPh | |
| H | H | CO$_2$t-Bu | Cl | CR$^6$ | N | —NH—CH$_2$Ph | |
| H | H | CO$_2$t-Bu | Cl | CR$^6$ | N | —NH—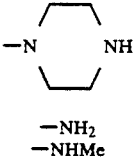 | |
| H | H | CO$_2$t-Bu | Cl | CR$^6$ | N | —NH-i-Pr | |
| H | H | CO$_2$t-Bu | Cl | CR$^6$ | N | —NH—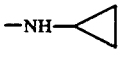 | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | $CO_2$t-Bu | Cl | $CR^6$ | N | —NH—cyclohexyl | |
| H | H | $CO_2$t-Bu | Cl | $CR^6$ | N | —$NMe_2$ | |
| H | H | $CO_2$t-Bu | Cl | $CR^6$ | N | —$NEt_2$ | |
| H | H | $CO_2$t-Bu | Cl | $CR^6$ | N | —$N(iPr)_2$ | |
| H | H | $CO_2$t-Bu | Cl | $CR^6$ | N | —N(piperidinyl) | |
| H | H | $CO_2$t-Bu | Cl | $CR^6$ | N | —N(pyrrolidinyl) | |
| H | H | $CO_2$t-Bu | Cl | $CR^6$ | N | —N(azetidinyl) | |
| H | H | $CO_2$t-Bu | Cl | $CR^6$ | N | —N(pyrrolyl) | |
| H | H | $CO_2$t-Bu | Cl | $CR^6$ | N | —N(morpholinyl) | |
| H | H | $CO_2$t-Bu | Cl | $CR^6$ | N | —N(piperazinyl)NH | |
| Me | Me | H | H | N | $CR^6$ | —$NH_2$ | |
| Me | Me | H | H | N | $CR^6$ | —NHMe | |
| Me | Me | H | H | N | $CR^6$ | —NHEt | |
| Me | Me | H | H | N | $CR^6$ | —NHPh | |
| Me | Me | H | H | N | $CR^6$ | —NH—$CH_2$Ph | |
| Me | Me | H | H | N | $CR^6$ | —NH—cyclopropyl | |
| Me | Me | H | H | N | $CR^6$ | —NH-i-Pr | |
| Me | Me | H | H | N | $CR^6$ | —NH—cyclopentyl | |
| Me | Me | H | H | N | $CR^6$ | —NH—cyclohexyl | |
| Me | Me | H | H | N | $CR^6$ | —$NMe_2$ | |
| Me | Me | H | H | N | $CR^6$ | —$NEt_2$ | |
| Me | Me | H | H | N | $CR^6$ | —$N(iPr)_2$ | |
| Me | Me | H | H | N | $CR^6$ | —N(piperidinyl) | |

TABLE-continued

| | | | (T = SO; A as defined above under (b); $R^4$; $R^5$ and $R^9$ each = hydrogen) | | | | |
|---|---|---|---|---|---|---|---|
| $R^1$ | $R^2$ | $R^3$ | $R^6$ | X | Y | Z | $R^{10}$ |
| Me | Me | H | H | N | $CR^6$ | pyrrolidin-1-yl | |
| Me | Me | H | H | N | $CR^6$ | azetidin-1-yl | |
| Me | Me | H | H | N | $CR^6$ | pyrrol-1-yl | |
| Me | Me | H | H | N | $CR^6$ | morpholin-4-yl | |
| Me | Me | H | H | N | $CR^6$ | piperazin-1-yl | |
| Me | Me | H | H | $CR^6$ | N | —$NH_2$ | |
| Me | Me | H | H | $CR^6$ | N | —NHMe | |
| Me | Me | H | H | $CR^6$ | N | —NHEt | |
| Me | Me | H | H | $CR^6$ | N | —NHPh | |
| Me | Me | H | H | $CR^6$ | N | —NH—$CH_2$Ph | |
| Me | Me | H | H | $CR^6$ | N | —NH-cyclopropyl | |
| Me | Me | H | H | $CR^6$ | N | —NH-i-Pr | |
| Me | Me | H | H | $CR^6$ | N | —NH-cyclopentyl | |
| Me | Me | H | H | $CR^6$ | N | —NH-cyclohexyl | |
| Me | Me | H | H | $CR^6$ | N | —$NMe_2$ | |
| Me | Me | H | H | $CR^6$ | N | —$NEt_2$ | |
| Me | Me | H | H | $CR^6$ | N | —N(iPr)$_2$ | |
| Me | Me | H | H | $CR^6$ | N | piperidin-1-yl | |
| Me | Me | H | H | $CR^6$ | N | pyrrolidin-1-yl | |
| Me | Me | H | H | $CR^6$ | N | azetidin-1-yl | |

TABLE-continued

| | | | | (T = SO; A as defined above under (b); $R^4$; $R^5$ and $R^9$ each = hydrogen) | | | |
|---|---|---|---|---|---|---|---|
| $R^1$ | $R^2$ | $R^3$ | $R^6$ | X | Y | Z | $R^{10}$ |
| Me | Me | H | H | $CR^6$ | N | —N(pyrrole) | |
| Me | Me | H | H | $CR^6$ | N | —N(morpholine) | |
| Me | Me | H | H | $CR^6$ | N | —N(piperazine-NH) | |
| H | H | H | —O—CH$_2$—C$_6$H$_4$—F (4-fluorobenzyloxy) | N | $CR^6$ | —NH$_2$ | |
| H | H | H | " | N | $CR^6$ | —NHMe | |
| H | H | H | " | N | $CR^6$ | —NHEt | |
| H | H | H | " | N | $CR^6$ | —NHPh | |
| H | H | H | " | N | $CR^6$ | —NH—CH$_2$Ph | |
| H | H | H | " | N | $CR^6$ | —NH-cyclopropyl | |
| H | H | H | " | N | $CR^6$ | —NH-i-Pr | |
| H | H | H | " | N | $CR^6$ | —NH-cyclopentyl | |
| H | H | H | " | N | $CR^6$ | —NH-cyclohexyl | |
| H | H | H | " | N | $CR^6$ | —NMe$_2$ | |
| H | H | H | " | N | $CR^6$ | —NEt$_2$ | |
| H | H | H | " | N | $CR^6$ | —N(iPr)$_2$ | |
| H | H | H | " | N | $CR^6$ | —N(piperidine) | |
| H | H | H | " | N | $CR^6$ | —N(pyrrolidine) | |
| H | H | H | " | N | $CR^6$ | —N(azetidine) | |
| H | H | H | " | N | $CR^6$ | —N(pyrrole) | |
| H | H | H | " | N | $CR^6$ | —N(morpholine) | |

TABLE-continued

| | | | (T = SO; A as defined above under (b); R⁴; R⁵ and R⁹ each = hydrogen) | | | | |
|---|---|---|---|---|---|---|---|
| $R^1$ | $R^2$ | $R^3$ | $R^6$ | X | Y | Z | $R^{10}$ |
| H | H | H | " | N | $CR^6$ | —N⟨piperazine-NH⟩ | |
| H | H | H | O–CH₂Ph | N | $CR^6$ | —NH₂ | |
| H | H | H | " | N | $CR^6$ | —NHMe | |
| H | H | H | " | N | $CR^6$ | —NHEt | |
| H | H | H | " | N | $CR^6$ | —NHPh | |
| H | H | H | " | N | $CR^6$ | —NH—CH₂Ph | |
| H | H | H | " | N | $CR^6$ | —NH—cyclopropyl | |
| H | H | H | " | N | $CR^6$ | —NH-i-Pr | |
| H | H | H | " | N | $CR^6$ | —NH—cyclopentyl | |
| H | H | H | " | N | $CR^6$ | —NH—cyclohexyl | |
| H | H | H | " | N | $CR^6$ | —NMe₂ | |
| H | H | H | " | N | $CR^6$ | —NEt₂ | |
| H | H | H | " | N | $CR^6$ | —N(iPr)₂ | |
| H | H | H | " | N | $CR^6$ | —N(piperidine) | |
| H | H | H | " | N | $CR^6$ | —N(pyrrolidine) | |
| H | H | H | " | N | $CR^6$ | —N(azetidine) | |
| H | H | H | " | N | $CR^6$ | —N(pyrrole) | |
| H | H | H | " | N | $CR^6$ | —N(morpholine) | |
| H | H | H | " | N | $CR^6$ | —N(piperazine-NH) | |
| H | H | H | O–CH₂CF₂CF₂CF₃ | N | $CR^6$ | —NH₂ | |
| H | H | H | " | N | $CR^6$ | —NHMe | |
| H | H | H | " | N | $CR^6$ | —NHEt | |
| H | H | H | " | N | $CR^6$ | —NHPh | |

TABLE-continued

(T = SO; A as defined above under (b); R⁴; R⁵ and R⁹ each = hydrogen)

| $R^1$ | $R^2$ | $R^3$ | $R^6$ | X | Y | Z | $R^{10}$ |
|---|---|---|---|---|---|---|---|
| H | H | H | " | N | $CR^6$ | —NH—CH₂Ph | |
| H | H | H | " | N | $CR^6$ | —NH—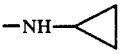 | |
| H | H | H | " | N | $CR^6$ | —NH-i-Pr | |
| H | H | H | " | N | $CR^6$ | —NH—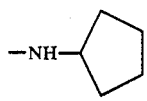 | |
| H | H | H | " | N | $CR^6$ | —NH—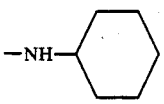 | |
| H | H | H | " | N | $CR^6$ | —NMe₂ | |
| H | H | H | " | N | $CR^6$ | —NEt₂ | |
| H | H | H | " | N | $CR^6$ | —N(iPr)₂ | |
| H | H | H | " | N | $CR^6$ | 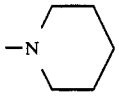 | |
| H | H | H | " | N | $CR^6$ | 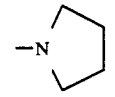 | |
| H | H | H | " | N | $CR^6$ | 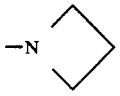 | |
| H | H | H | " | N | $CR^6$ | 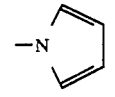 | |
| H | H | H | " | N | $CR^6$ | 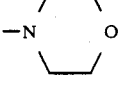 | |
| H | H | H | " | N | $CR^6$ | 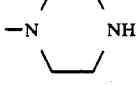 | |
| H | H | H | 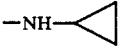 | N | $CR^6$ | —NH₂ | |
| H | H | H | " | N | $CR^6$ | —NHMe | |
| H | H | H | " | N | $CR^6$ | —NHEt | |
| H | H | H | " | N | $CR^6$ | —NHPh | |
| H | H | H | " | N | $CR^6$ | —NH—CH₂Ph | |
| H | H | H | " | N | $CR^6$ | —NH—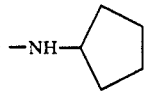 | |
| H | H | H | " | N | $CR^6$ | —NH-i-Pr | |
| H | H | H | " | N | $CR^6$ | —NH—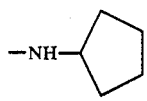 | |

TABLE-continued

| | | | (T = SO; A as defined above under (b); R⁴; R⁵ and R⁹ each = hydrogen) | | | | |
|---|---|---|---|---|---|---|---|
| $R^1$ | $R^2$ | $R^3$ | $R^6$ | X | Y | Z | $R^{10}$ |
| H | H | H | " | N | $CR^6$ | —NH—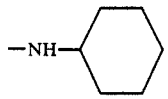 | |
| H | H | H | " | N | $CR^6$ | —NMe₂ | |
| H | H | H | " | N | $CR^6$ | —NEt₂ | |
| H | H | H | " | N | $CR^6$ | —N(iPr)₂ | |
| H | H | H | " | N | $CR^6$ |  | |
| H | H | H | " | N | $CR^6$ |  | |
| H | H | H | " | N | $CR^6$ |  | |
| H | H | H | " | N | $CR^6$ | 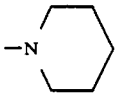 | |
| H | H | H | " | N | $CR^6$ | 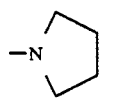 | |
| H | H | H | " | N | $CR^6$ | 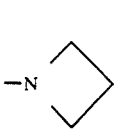 | |
| H | H | H |  | $CR^6$ | N | —NH₂ | |
| H | H | H | " | $CR^6$ | N | —NHMe | |
| H | H | H | " | $CR^6$ | N | —NHEt | |
| H | H | H | " | $CR^6$ | N | —NHPh | |
| H | H | H | " | $CR^6$ | N | —NH—CH₂Ph | |
| H | H | H | " | $CR^6$ | N | —NH—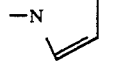 | |
| H | H | H | " | $CR^6$ | N | —NH-i-Pr | |
| H | H | H | " | $CR^6$ | N | —NH—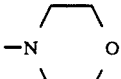 | |
| H | H | H | " | $CR^6$ | N | —NH— | |
| H | H | H | " | $CR^6$ | N | —NMe₂ | |
| H | H | H | " | $CR^6$ | N | —NEt₂ | |
| H | H | H | " | $CR^6$ | N | —N(iPr)₂ | |

TABLE-continued
(T = SO; A as defined above under (b); R⁴; R⁵ and R⁹ each = hydrogen)
| R¹ | R² | R³ | R⁶ | X | Y | Z | R¹⁰ |
|----|----|----|----|----|----|----|----|
| H | H | H | " | CR⁶ | N | 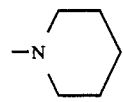 | |
| H | H | H | " | CR⁶ | N | 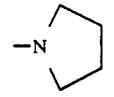 | |
| H | H | H | " | CR⁶ | N | 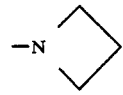 | |
| H | H | H | " | CR⁶ | N | 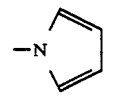 | |
| H | H | H | " | CR⁶ | N | 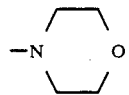 | |
| H | H | H | " | CR⁶ | N | 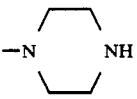 | |
| H | H | H | O-CH₂-CF₂CF₂CF₃ | CR⁶ | N | —NH₂ | |
| H | H | H | " | CR⁶ | N | —NHMe | |
| H | H | H | " | CR⁶ | N | —NHEt | |
| H | H | H | " | CR⁶ | N | —NHPh | |
| H | H | H | " | CR⁶ | N | —NH—CH₂Ph | |
| H | H | H | " | CR⁶ | N | 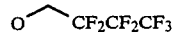 | |
| H | H | H | " | CR⁶ | N | —NH-i-Pr | |
| H | H | H | " | CR⁶ | N | 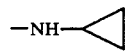 | |
| H | H | H | " | CR⁶ | N | 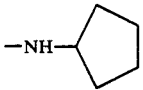 | |
| H | H | H | " | CR⁶ | N | —NMe₂ | |
| H | H | H | " | CR⁶ | N | —NEt₂ | |
| H | H | H | " | CR⁶ | N | —N(iPr)₂ | |
| H | H | H | " | CR⁶ | N | 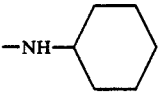 | |
| H | H | H | " | CR⁶ | N | 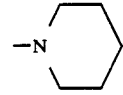 | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | H | | $CR^6$ | N | −N(azetidinyl) | |
| H | H | H | | $CR^6$ | N | −N(pyrrolyl) | |
| H | H | H | | $CR^6$ | N | −N(morpholinyl) | |
| H | H | H | | $CR^6$ | N | −N(piperazinyl)NH | |
| H | H | H | −O−CH₂−(4-F-C₆H₄) | $CR^6$ | N | −NH₂ | |
| H | H | H | " | $CR^6$ | N | −NHMe | |
| H | H | H | " | $CR^6$ | N | −NHEt | |
| H | H | H | " | $CR^6$ | N | −NHPh | |
| H | H | H | " | $CR^6$ | N | −NH−CH₂Ph | |
| H | H | H | " | $CR^6$ | N | −NH−cyclopropyl | |
| H | H | H | " | $CR^6$ | N | −NH-i-Pr | |
| H | H | H | " | $CR^6$ | N | −NH−cyclopentyl | |
| H | H | H | " | $CR^6$ | N | −NH−cyclohexyl | |
| H | H | H | " | $CR^6$ | N | −NMe₂ | |
| H | H | H | " | $CR^6$ | N | −NEt₂ | |
| H | H | H | " | $CR^6$ | N | −N(iPr)₂ | |
| H | H | H | " | $CR^6$ | N | −N(piperidinyl) | |
| H | H | H | " | $CR^6$ | N | −N(pyrrolidinyl) | |
| H | H | H | " | $CR^6$ | N | −N(azetidinyl) | |
| H | H | H | " | $CR^6$ | N | −N(pyrrolyl) | |

TABLE-continued (T = SO; A as defined above under (b); R⁴; R⁵ and R⁹ each = hydrogen)

| R¹ | R² | R³ | R⁶ | X | Y | Z | R¹⁰ |
|---|---|---|---|---|---|---|---|
| H | H | H | " | CR⁶ | N | morpholino (—N(CH₂CH₂)₂O) | |
| H | H | H | " | CR⁶ | N | piperazinyl (—N(CH₂CH₂)₂NH) | |
| H | H | H | O-Ph | CR⁶ | N | —NH₂ | |
| H | H | H | " | CR⁶ | N | —NHMe | |
| H | H | H | " | CR⁶ | N | —NHEt | |
| H | H | H | " | CR⁶ | N | —NHPh | |
| H | H | H | " | CR⁶ | N | —NH—CH₂Ph | |
| H | H | H | " | CR⁶ | N | —NH-cyclopropyl | |
| H | H | H | " | CR⁶ | N | —NH-i-Pr | |
| H | H | H | " | CR⁶ | N | —NH-cyclopentyl | |
| H | H | H | " | CR⁶ | N | —NH-cyclohexyl | |
| H | H | H | " | CR⁶ | N | —NMe₂ | |
| H | H | H | " | CR⁶ | N | —NEt₂ | |
| H | H | H | " | CR⁶ | N | —N(iPr)₂ | |
| H | H | H | " | CR⁶ | N | piperidino | |
| H | H | H | " | CR⁶ | N | pyrrolidino | |
| H | H | H | " | CR⁶ | N | azetidino | |
| H | H | H | " | CR⁶ | N | pyrrolyl | |
| H | H | H | " | CR⁶ | N | morpholino | |
| H | H | H | " | CR⁶ | N | piperazinyl | |
| H | H | H | OCH₃ | CR⁶ | N | —NH₂ | |
| H | H | H | OCH₃ | CR⁶ | N | —NHMe | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | H | OCH$_3$ | CR$^6$ | N | —NHEt | |
| H | H | H | OCH$_3$ | CR$^6$ | N | —NHPh | |
| H | H | H | OCH$_3$ | CR$^6$ | N | —NH—CH$_2$Ph | |
| H | H | H | OCH$_3$ | CR$^6$ | N | —NH—cyclopropyl 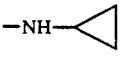 | |
| H | H | H | OCH$_3$ | CR$^6$ | N | —NH-i-Pr | |
| H | H | H | OCH$_3$ | CR$^6$ | N | —NH—cyclopentyl 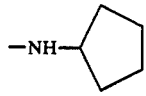 | |
| H | H | H | OCH$_3$ | CR$^6$ | N | —NH—cyclohexyl 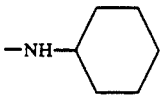 | |
| H | H | H | OCH$_3$ | CR$^6$ | N | —NMe$_2$ | |
| H | H | H | OCH$_3$ | CR$^6$ | N | —NEt$_2$ | |
| H | H | H | OCH$_3$ | CR$^6$ | N | —N(iPr)$_2$ | |
| H | H | H | OCH$_3$ | CR$^6$ | N | —piperidinyl 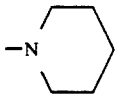 | |
| H | H | H | OCH$_3$ | CR$^6$ | N | —pyrrolidinyl  | |
| H | H | H | OCH$_3$ | CR$^6$ | N | —azetidinyl  | |
| H | H | H | OCH$_3$ | CR$^6$ | N | —pyrrolyl 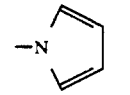 | |
| H | H | H | OCH$_3$ | CR$^6$ | N | —morpholinyl  | |
| H | H | H | OCH$_3$ | CR$^6$ | N | —piperazinyl  | |
| H | H | H | OCH$_3$ | N | CR$^6$ | —NH$_2$ | |
| H | H | H | OCH$_3$ | N | CR$^6$ | —NHMe | |
| H | H | H | OCH$_3$ | N | CR$^6$ | —NHEt | |
| H | H | H | OCH$_3$ | N | CR$^6$ | —NHPh | |
| H | H | H | OCH$_3$ | N | CR$^6$ | —NH—CH$_2$Ph | |
| H | H | H | OCH$_3$ | N | CR$^6$ | —NH—cyclopropyl 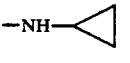 | |
| H | H | H | OCH$_3$ | N | CR$^6$ | —NH-i-Pr | |
| H | H | H | OCH$_3$ | N | CR$^6$ | —NH—cyclopentyl 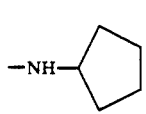 | |

TABLE-continued (T = SO; A as defined above under (b); $R^4$; $R^5$ and $R^9$ each = hydrogen)

| $R^1$ | $R^2$ | $R^3$ | $R^6$ | X | Y | Z | $R^{10}$ |
|---|---|---|---|---|---|---|---|
| H | H | H | OCH₃ | N | CR⁶ | —NH—⟨cyclohexyl⟩ | |
| H | H | H | OCH₃ | N | CR⁶ | —NMe₂ | |
| H | H | H | OCH₃ | N | CR⁶ | —NEt₂ | |
| H | H | H | OCH₃ | N | CR⁶ | —N(iPr)₂ | |
| H | H | H | OCH₃ | N | CR⁶ | —N⟨piperidinyl⟩ | |
| H | H | H | OCH₃ | N | CR⁶ | —N⟨pyrrolidinyl⟩ | |
| H | H | H | OCH₃ | N | CR⁶ | —N⟨azetidinyl⟩ | |
| H | H | H | OCH₃ | N | CR⁶ | —N⟨pyrrolyl⟩ | |
| H | H | H | OCH₃ | N | CR⁶ | —N⟨morpholinyl⟩ | |
| H | H | H | OCH₃ | N | CR⁶ | —N⟨piperazinyl⟩NH | |

The new compounds of the formula I and their salts have valuable pharmacological properties.

They distinctly inhibit gastric acid secretion and, furthermore, have an excellent gastrointestinal protective action.

"Gastrointestinal protection" in this connection is to be understood to be the prevention and treatment of gastrointestinal disorders, especially inflammatory gastrointestinal disorders and lesions (such as, for example, gastric ulcer, duodenal ulcer, gastritis, and functional gastropathy due to hyperacidity or drug-related), which can be caused, for example, by microorganisms, bacteriotoxins, drugs (for example antiinflammatory and antirheumatic agents), chemicals (for example ethanol), gastric acid or stress situations.

By reason of their excellent properties, the substituted thienoimidazoles of the formula I and their pharmacologically tolerated salts are outstandingly suitable for use in human and veterinary medicine, being used, in particular, for the treatment and prophylaxis of disorders of the stomach and intestines and those disorders deriving from excessive gastric acid secretion.

It has been found that colon H⁺/K⁺ ATPase (cf. Gustin, Goodman, J. Biol. Chem. 256 [1981]10651–10656) is also strongly inhibited in vitro by compounds which are produced on treatment of the compounds of the formula I, according to the invention, with acid (for example with sodium acetate/HCl buffer with a pH of about 4–5.5). Transformation products of this type may also be formed in vivo on passage of the compounds of the formula I through the gastrointestinal tract. The extent to which they are formed depends on the substitution pattern and on the pH.

Colon H⁺/K⁺ ATPase is attributed with a crucial influence on the electrolyte balance on the intestinal mucosa. Hence, inhibitors of colon H⁺/K⁺ ATPase, such as those mentioned above, may intervene in this equilibrium and be used for treating disorders where the electrolyte balance is disturbed.

Hence the invention also relates to the use of compounds of the formula I, or their acid transformation products, for the treatment of diarrheal disorders. Examples of such disorders are inflammatory intestinal disorders such as cholera, paratyphoid, travelers' diarrhea or other types of secretory diarrhea, as well as other intestinal disorders such as ulcerative colitis and regional enteritis.

Hence the invention furthermore relates to the compounds of the formula I, according to the invention, for use for the treatment and prophylaxis of the abovementioned disorders.

The invention likewise embraces the use of the compounds according to the invention for the preparation of pharmaceuticals used for the treatment and prophylaxis of the abovementioned disorders.

The invention further relates to pharmaceuticals which contain one or more compounds of the general formula I and/or their pharmacologically tolerated salts.

The pharmaceuticals are prepared by processes which are known per se and familiar to the expert. As pharmaceuticals, the pharmacologically active compounds (=active substances) according to the invention are used either as such or, preferably, in combination with suitable pharmaceutical auxiliaries in the form of tablets, coated tablets, capsules, suppositories, emulsions, suspensions or solutions, with the content of active substance advantageously being between 0.1 and 96%.

The auxiliaries suitable for the desired pharmaceutical formulations are familiar to the expert on the basis of his knowledge. Besides solvents, gel-forming agents, suppository bases, tableting auxiliaries and other active substance vehicles, it is possible to use, for example, antioxidants, dispersing agents, emulsifiers, antifoam agents, masking flavors, preservatives, solubilizers or colorants.

The active substances can be administered orally or parenterally, with oral administration being preferred.

In general, it has proved advantageous in human medicine, in the case of oral administration, for the active substance(s) to be administered in a daily dose of about 0.01 to about 20 mg/kg of bodyweight, where appropriate in the form of several, preferably 1 to 4, single doses to achieve the desired result. In the case of parenteral administration, the dosages which can be used are similar or (especially in the case of intravenous administration of the active substances) as a rule lower. Every expert will be able easily to establish, on a basis of his expert knowledge, the optimal dosage and mode of administration of the active substances necessary in each case.

If the compounds according to the invention and/or their salts are to be used for the treatment of the abovementioned disorders, it is also possible for the pharmaceutical formulations to contain one or more pharmacologically active ingredients from other groups of pharmaceuticals, such as antibiotics, antacids, for example aluminum hydroxide, magnesium aluminate, sucralfate, bi salts; tranquilizers such as benzodiazepines, for example diazepam; spasmolytics such as, for example, bietamiverine, camylofin; anticholinergics such as, for example, pirenzepine, telenzepine, oxyphencylimine, phencarbamide; local anesthetics such as, for example, tetracaine, procaine; and, where appropriate, gastrin antagonists, enzymes, vitamins or amino acids. For a form for oral administration, the active compounds are mixed with the additives suitable for this purpose, such as vehicles, stabilizers or inert diluents and converted by customary methods into suitable dosage forms, such as tablets, coated tablets, hard gelatine capsules, aqueous, alcoholic or oily suspensions or aqueous, alcoholic or oily solutions.

Examples of inert vehicles which can be used are gum arabic, magnesia, magnesium carbonate, lactose, glucose or starch, especially corn starch. In this connection, formulation can be effected both as dry and wet granules. Examples of suitable oily vehicles or solvents are vegetable and animal oils, such as sunflower oil or fish liver oil.

For subcutaneous or intravenous administration, the active compounds or their physiologically tolerated salts are converted into a solution, suspension or emulsion, if desired with the substances customary for this purpose, such as solubilizers, emulsifiers or further auxiliaries. Examples of suitable solvents for the new active compounds and the corresponding physiologically tolerated salts are: water, physiological saline solutions or alcohols, for example ethanol, propanol or glycerol, as well as sugar solutions such as glucose or mannitol solutions, or else a mixture of the various solvents mentioned.

The examples which follow serve to illustrate the invention without intending to confine it thereto.

EXAMPLE 1

2-[4-Morpholino-2-pyrimidinylmethylsulfinyl]-1H-thieno[3,4-d]imidazole (a) A mixture of 120 g of methoxyacetamidine hydrochloride and 300 g of ethyl formylacetate sodium salt in 1.5 l of water was stirred at room temperature for 3 days.

The reaction solution was concentrated and then acidified with hydrochloric acid and extracted with hydrochloric acid and extracted with dichloromethane. Purification by column chromatography resulted in 100 g of 2-methoxymethyl-4-pyrimidone (melting point 126° C.).

(b) A suspension of 100 g of 2-methoxymethyl-4-pyrimidone and 500 ml of phosphorus oxychloride was slowly heated until a clear solution formed. Excess phosphorus oxychloride was distilled, the residue was hydrolyzed with ice-water, and the pH was adjusted to 10 with sodium hydroxide solution. Extraction with dichloromethane followed by purification by column chromatography resulted in 101 g of 2-methoxymethyl-4-chloropyrimidine as an oil.

(c) A solution of 12 g of 2-methoxymethyl-4-chloropyrimidine and 15 ml of morpholine in 50 ml of dichloromethane was stirred at room temperature for 3 hours. The reaction solution was washed several times with water. The organic phase was dried and, after purification by column chromatography, yielded 13 g of 2-methoxymethyl4-morpholinopyrimidine as an oil.

(d) A solution of 24 ml of boron tribromide in 100 ml of dichloromethane was added dropwise, at −25° C. under a nitrogen atmosphere, to a solution of 13 g of 2-methoxymethyl-4-morpholinopyrimidine in 100 ml of dichloromethane. After 30 minutes at −25° C., the solution was left to stand at 0° C. for a further 2 hours and then poured onto ice. The solution was made alkaline with sodium hydroxide solution and was extracted with dichloromethane. After drying (Na$_2$SO$_4$) and concentration, diethyl ether was added, and 5.5 g of 2-hydroxymethyl-4-morpholinopyrimidine were obtained as a solid (melting point 76°–77° C.).

(e) A solution of 5.5 g of 2-hydroxymethyl-4-morpholinopyrimidine and 17 ml of thionyl chloride in 200 ml of dichloromethane was stirred at room temperature for 3 hours. After concentration, diethyl ether was added, and the precipitated 2-chloromethyl-4-morpholinopyrimidine hydrochloride was filtered off (yield 6.0 g; melting point 215° C.).

(f) A mixture of 1 g of sodium methylate, 1.3 g of 2-mercaptothieno[3,4-d]imidazole and 2 g of 2-chloromethyl4-morpholinopyrimidine hydrochloride in 50 ml of methanol was heated under reflux for 2 hours.

The mixture was then poured onto ice-water and extracted with dichloromethane. Purification by column chromatography resulted in 1.6 g of 2-(4-morpholino-2-pyrimidinylmethylthio)thieno[3,4-d]imidazole as a solid (melting point 185° C. [decomposition]).

(g) 200 mg of m-chloroperbenzoic acid were added in portions to a suspension of 300 mg of 2-(4-morpholino-2-pyrimidinylmethylthio)-1H-thieno[3,4-d]imidazole in a mixture of 30 ml of dichloromethane and 30 ml of sodium bicarbonate solution at 0° C. After 30 minutes, the Na salt of 2-(4-morpholino-2-pyrimidinylmethylsulfinyl)1H-thieno-[3,4-d]imidazole separated out between the phases and was filtered off and washed with dichloromethane (yield: 300 mg; melting point 165° C. [decomposition]).

(h) 300 mg of the Na salt of 2-(4-morpholino-2-pyrimidinylmethylsulfinyl)-1H-thieno[3,4-d]imidazole were suspended in a mixture of 10 ml of dichloromethane and 10 ml of water, and the pH was adjusted to 6 with saturated ammonium chloride solution. The aqueous phase was extracted with dichloromethane, and the organic phase was dried ($Na_2SO_4$) and concentrated. Radial layer chromatography resulted in 200 mg of 2-(4-morpholino-2-pyrimidinylmethylsulfinyl)-1H-thieno[3,4-d]imidazole as a solid (melting point 164° C. [decomposition]).

The following compounds were obtained in an analogous manner:

EXAMPLE 2

2-[4-Piperidino-2-pyrimidinylmethylthio]-1H-thieno[3,4-d]imidazole, melting point 197° C. [decomposition]

EXAMPLE 3

2-[4-N,N-Dimethylamino-2-pyrimidinylmethylthio]-1H-thieno[3,4-d]imidazole, melting point 193° C. [decomposition]

EXAMPLE 4

2-[5-Methyl-4-morpholino-2-pyrimidinylmethylthio]-1H-thieno[3,4-d]imidazole, melting point 177° C. [decomposition]

EXAMPLE 5

2-[5-Methyl-4-piperidino-2-pyrimidinylmethylthio]-1H-thieno[3,4-d]imidazole, melting point 117° C. [decomposition]

EXAMPLE 6

2-[5-Methyl-4-piperazino-2-pyrimidinylmethylthio]-1H-thieno[3,4-d]imidazole, melting point 230° C. [decomposition]

EXAMPLE 7

2-[5-Methyl-4-(4-methylphenylamino)-2-pyrimidinylmethylthio]-1H-thieno[3,4-d]imidazole, melting point 77° C. [decomposition]

EXAMPLE 8

2-[5-Methyl-4-(4-methylphenylamino)-2-pyrimidinylmethylsulfinyl]-1H-thieno[3,4-d]imidazole, melting point 115° C. [decomposition]

EXAMPLE 9

2-(5-Chloro-4-piperidino-2-pyrimidinylmethylthio)-1H-thieno[3,4-d]imidazole, melting point 132° C. [decomposition]

EXAMPLE 10

2-(5-Chloro-4-piperidino-2-pyrimidinylmethylsulfinyl)-1H-thieno[3,4-d]imidazole, melting point 59° C. [decomposition]

EXAMPLE 11

2-(5-Chloro-4-morpholino-2-pyrimidinylmethylthio)-1H-thieno[3,4-d]imidazole, melting point 165° C. [decomposition]

EXAMPLE 12

2-(5-Chloro-4-morpholino-2-pyrimidinylmethylsulfinyl)-1H-thieno[3,4-d]imidazole, melting point 81° C. [decomposition]

EXAMPLE 13

2-(5-Chloro-4-morpholino-2-pyrimidinylmethylsulfonyl)-1H-thieno[3,4-d]imidazole, melting point 155° C. [decomposition]

EXAMPLE 14

2-[5-Methyl-4-(4-methyl-1-piperazinyl)-2-pyrimidinylmethylthio]-1H-thieno[3,4-d]imidazole, melting point 159° C. [decomposition]

EXAMPLE 15

2-(5-Chloro-4-pyrrolidino-2-pyrimidinylmethylthio)-1H-thieno[3,4-d]imidazole, melting point 188° C. [decomposition]

EXAMPLE 16

2-(5-Chloro-4-pyrrolidino-2-pyrimidinylmethylsulfinyl)-1H-thieno[3,4-d]imidazole, melting point 86° C. [decomposition]

EXAMPLE 17

2-[5-Chloro-4-(N,N-dimethylamino)-2-pyrimidinylmethylsulfinyl]-1H-thieno[3,4-d]imidazole, melting point 178° C. [decomposition]

EXAMPLE 18

2-[5-Chloro-4-(N,N-dimethylamino)-2-pyrimidinylmethylsulfinyl]-1H-thieno[3,4-d]imidazole, melting point 112° C. [decomposition]

EXAMPLE 19

2-(4-Benzylpiperidino-5-chloro-2-pyrimidinylmethylsulfonyl)-1H-thieno[3,4-d]imidazole, melting point 166° C. [decomposition]

EXAMPLE 20

2-(4-Methoxy-2-pyrimidinylmethylsulfinyl)-1H-thieno[3,4-d]imidazole (a) 650 g of ethyl formylacetate sodium salt were dissolved in 4 l of cold water, and 450 g of acetamidine hydrochloride were added. After the solution had stood at room temperature for two days it was evaporated to dryness in vacuo, and the residue was extracted with hot ethanol. Concentration of the ethanolic extracts and purification by column chromatography resulted in 240 g of 2-methyl-4-pyrimidone (melting point 212° C.).

(b) 11 g of 2-methyl-4-pyrimidone were introduced into 50 ml of phosphorus oxychloride, and the mixture was heated at 80° C. until a clear solution was produced. Excess phosphorus oxychloride was removed by distillation in vacuo, and the residue was poured into ice-water. While cooling, the solution was neutralized with potassium hydroxide solution and extracted with dichloromethane. The organic extracts were dried (Na$_2$SO$_4$) and concentrated in vacuo, and column chromatography resulted in 8 g of 4-chloro-2-methylpyrimidine (melting point 50°-60° C.).

(c) 6.5 g of 4-chloro-2-methylpyrimidine were added to a solution of 1.2 g of sodium in 50 ml of absolute methanol. The reaction mixture was heated under reflux for 1 hour and then concentrated in vacuo, water was added and extraction with diethyl ether was carried out. Column chromatography resulted in 6 g of 4-methoxy-2methylpyrimidine as an oil.

(d) A suspension of 6 g of 4-methoxy-2-methylpyrimidine and 4 g of trichloroisocyanuric acid in 50 ml of carbon tetrachloride was heated under reflux. After the reaction was complete, water was added, the pH was adjusted to 8 to 9, and the mixture was extracted with dichloromethane. Column chromatography resulted in 4 g of 2-chloromethyl-4-methoxypyrimidine as an oil.

(e) 900 mg of sodium hydride suspension (55 %) and, after 15 minutes, 3.3 g of 2-chloromethyl-4-methoxypyrimidine were added to a solution of 3.1 g of 2-mercaptothieno[3,4-d]imidazole in 100 ml of absolute dimethylformamide at room temperature. The reaction mixture was then stirred at room temperature for 1 hour, poured onto ice and extracted with dichloromethane. Drying (Na$_2$SO$_4$) and concentration of the organic phase was followed by purification on a silica gel column, resulting in 1.6 g of 2-(4-methoxy-2-pyrimidinylmethylthio)-1H-thieno[3,4-d]imidazole (melting point 165° C. [decomposition]).

(f) 1.1 g of 2-(4-methoxy-2-pyrimidinylmethylthio)-1H-thieno[3,4-d]imidazole were dissolved in 100 ml of dichloromethane and, at −10° C., 820 mg of m-chloroperbenzoic acid were added in portions. The mixture was then stirred at room temperature for 15 minutes, extracted by shaking with sodium bicarbonate solution, and the organic phase was dried over sodium sulfate and concentrated. Purification by chromatography resulted in 300 mg of 2-(4-methoxy-2-pyrimidinylmethylsulfinyl)1H-thieno[3,4-d]imidazole (melting point 125° C. [decomposition]).

The following compounds were obtained in analogy to Example 20:

EXAMPLE 21

2-(4-Ethoxy-2-pyrimidinylmethylthio)-1H-thieno[3,4-d]imidazole, melting point 164° C. [decomposition]

EXAMPLE 22

2-(4-Ethoxy-2-pyrimidinylmethylsulfinyl)-1H-thieno[3,4-d]imidazole, melting point 115° C. [decomposition]

EXAMPLE 23

2-(4-Isopropoxy-2-pyrimidinylmethylthio)-1H-thieno[3,4-d]imidazole, melting point 182° C. [decomposition]

EXAMPLE 24

2-(4-Isopropoxy-2-pyrimidinylmethylsulfinyl)-1H-thieno- [3,4-d]imidazole, melting point 118° C. [decomposition]

EXAMPLE 25

2-(6-Morpholino-4-pyrimidinylmethylsulfinyl)-1H-thieno[3,4-d]imidazole (a) A solution of 86 g of sodium in 1.5 l of methanol was added to a solution of 250 g of methyl 4-methoxyacetoacetate and 200 g of formamidine acetate in 1.5 l of methanol. The reaction solution was heated at 60° C. for 48 hours, then concentrated in vacuo and poured into ice-water. Neutralization with hydrochloric acid was followed by extraction with dichloromethane, drying over sodium sulfate and concentration in vacuo. Purification on a silica gel column resulted in 100 g of 6-hydroxy-4-methoxymethylpyrimidine (melting point 160° C.).

(b) 50 g of 6-hydroxy-4-methoxymethylpyrimidine were heated in 375 ml of phosphorus oxychloride until a clear solution had been produced. The excess phosphorus oxychloride was removed by distillation in vacuo, and the residue was poured into ice-water. Extraction with dichloromethane and drying over sodium sulfate were followed by concentration of the solution in vacuo. 58 g of 6-chloro-4-methoxymethylpyrimidine were obtained as an oil which was used without further purification in the next stage.

(c) 29 g of 6-chloro-4-methoxymethylpyrimidine were dissolved in 200 ml of tetrahydrofuran, and 32 g of morpholine were added. After 3 hours at room temperature, the mixture was filtered with suction, and the filtrate was concentrated in vacuo.

37 g of 6-morpholino-4-methoxymethylpyrimidine were obtained (melting point 56° C.).

(d) 38 ml of 1M boron tribromide solution in CH$_2$Cl$_2$ were added dropwise, at 0° C., under a nitrogen atmosphere, to a solution of 5.3 g of 6-morpholino-4-methoxymethylpyrimidine in 100 ml of dichloromethane. The reaction solution was poured into ice-water, and the pH was adjusted to 13 with sodium hydroxide solution. Extraction with dichloromethane was followed by the organic phase being dried over sodium sulfate and concentrated in vacuo.

3 g of 4-hydroxymethyl-6-morpholinopyrimidine were obtained (melting point 138° C.).

(e) A solution of 36 ml of thionyl chloride in 30 ml of dichloromethane was added dropwise, at 0° C., to a solution of 3 g of 4-hydroxymethyl-6-morpholinopyrimidine in 30 ml of dichloromethane. The reaction solution was allowed to reach room temperature and was concentrated in vacuo. Addition of diethyl ether resulted in precipitation of 3.2 g of 4-chloromethyl-6-morpholinopyrimidine hydrochloride (melting point 139° C. [decomposition]).

(f) 1 g of 4-chloromethyl-6-morpholinopyrimidine hydrochloride was reacted with 625 mg of 2-mercaptothieno[[3,4-d]imidazole in analogy to the description in Example 1f. 420 mg of 2-(6-morpholino-4-pyrimidinylmethylthio)-1H-thieno[3,4-d]imidazole were obtained (melting point 178° C. [decomposition]).

(g) 180 mg of 2-(6-morpholino-4-pyrimidinylmethylthio)-1H-thieno[3,4-d]imidazole were oxidized with m-chloroperbenzoic acid in analogy to Example 1g. 140 mg of 2-(6-morpholino-4-pyrimidinylmethylsulfinyl)-1H-thieno[3,4-d]imidazole were obtained (melting point 107° C. [decomposition]).

The following compounds were obtained in an analogous manner:

EXAMPLE 26

2-(6-Piperidino-4-pyrimidinylmethylthio)-1H-thieno[3,4-d]imidazole, melting point 161° C. [decomposition].

EXAMPLE 27

2-(5-Chloro-6-piperidino-4-pyrimidinylmethylthio)-1H-thieno[3,4-d]imidazole, melting point 152° C. [decomposition]

EXAMPLE 28

2-(5-Chloro-6-piperidino-4-pyrimidinylmethylsulfinyl)-1H-thieno[3,4-d]imidazole, melting point 89° C. [decomposition]

EXAMPLE 29

2-(5-Chloro-6-morpholino-4-pyrimidinylmethylthio)-1H-thieno[3,4-d]imidazole, melting point 72° C. [decomposition]

EXAMPLE 30

2-(5-Chloro-6-morpholino-4-pyrimidinylmethylsulfinyl)-1H-thieno[3,4-d]imidazole, melting point 90° C. [decomposition]

EXAMPLE 31

2-(5-Methoxy-4-piperidino-2-pyrimidinylmethylsulfinyl)1H-thieno[3,4-d]imidazole (a) When the ethyl formylacetate sodium salt described in Example 1a is replaced by ethyl 2-methoxy-3-oxopropionate sodium salt, the product obtained correspondingly is 5-methoxy-2-methoxymethyl-4-pyrimidinone, melting point 61° C.

When the 5-methoxy-2-methoxymethyl-4-pyrimidinone is reacted further as described in Example 1b-g, the final stage obtained via intermediate stages 31b-f is 31g.

(b) 4-Chloro-5-methoxy-2-methoxymethylpyrimidine, oil (c) 5-Methoxy-2-methoxymethyl-4-piperidinopyrimidine, oil (d) 2-Hydroxy-5-methoxy-4-piperidinopyrimidine, melting point 102° C.

(e) 2-Chloromethyl-5-methoxy-4-piperidinopyrimidine hydrochloride, melting point 189° C. [decomposition]

(f) 2-(5-Methoxy-4-piperidino-2-pyrimidinylmethylthio)-1H-thieno[3,4-d]imidazole, melting point 103° C. [decomposition]

(g) 2-(5-Methoxy-4-piperidino-2-pyrimidinylmethylsulfinyl)-1H-thieno[3,4-d]imidazole, melting point 155° C. [decomposition]

EXAMPLE 32

2-(5-Methoxy-4-morpholino-2-pyrimidinylmethylsulfinyl)-1H-thieno[3,4-d]imidazole, melting point 130° C. [decomposition]

EXAMPLE 33

2-(5-Benzyloxy-4-morpholino-2-pyrimidinylmethylsulfinyl)-1H-thieno[3,4-d]imidazole, melting point 56° C. [decomposition]

EXAMPLE 34

2-[5-Benzyloxy-4-(4-benzylpiperidino)-2-pyrimidinylmethylsulfinyl]-1H-thieno[3,4-d]imidazole, melting point 62° C. [decomposition]

EXAMPLE 35

2-(5-Benzyloxy-4-piperidino-2-pyrimidinylmethylsulfinyl)-1H-thieno[3,4-d]imidazole, melting point 72° C. [decomposition]

EXAMPLE 36

2-[5-Benzyloxy-4-(N,N-dimethylamino)-2-pyrimidinylmethylsulfinyl]-1H-thieno[3,4-d]imidazole, melting point 65° C. [decomposition]

EXAMPLE 37

2-[5-(4-Fluorobenzyloxy)-4-(4-benzylpiperidino)-2-pyrimidinylmethylsulfinyl]-1H-thieno[3,4-d]imidazole, melting point 119° C. [decomposition]

EXAMPLE 38

2-[5-(4-Fluorobenzyloxy)-4-piperidino-2-pyrimidinylmethylsulfinyl]-1H-thieno[3,4-d]imidazole, melting point 110° C. [decomposition]

EXAMPLE 39

2-[5-(4-Fluorobenzyloxy)-4-morpholino-2-pyrimidinylmethylsulfinyl]-1H-thieno[3,4-d]imidazole, melting point 125° C. [decomposition]

EXAMPLE 40

2-[4-Piperidino-5-(2,2,2-trifluoroethoxy)-2-pyrimidinylmethylsulfinyl]-1H-thieno[3,4-d]imidazole, melting point 168° C. [decomposition]

EXAMPLE 41

2-[4-(N,N-Dimethylamino)-5-(2,2,2-trifluoroethoxy)-2-pyrimidinylmethylsulfinyl]-1H-thieno[3,4-d]imidazole, melting point 155° C. [decomposition]

EXAMPLE 42

2-[4-Morpholino-5-(2,2,2-trifluoroethoxy)-2-pyrimidinylmethylsulfinyl]-1H-thieno[3,4-d]imidazole, melting point 165° C. [decomposition]

EXAMPLE 43

2-[4-Pyrrolo-5-(2,2,2-trifluoroethoxy)-2-pyrimidinylmethylsulfinyl]-1H-thieno[3,4-d]imidazole, melting point 155° C. [decomposition]

EXAMPLE 44

2-[4-Piperidino-5-(4,4,4,3,3,2,2-heptafluorobutoxy)-2-pyrimidinylmethylsulfinyl]-1H-thieno[3,4-d]imidazole, melting point 172° C. [decomposition]

We claim:

1. A compound of the formula I

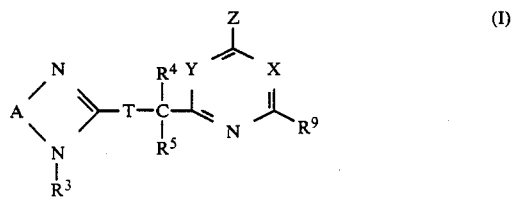

in which A represents

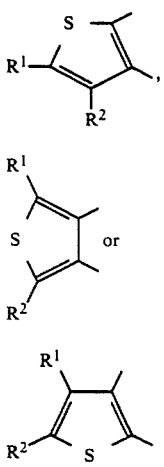

T denotes —S—, —SO— or —SO$_2$—,

R$^1$ and R$^2$ are identical or different and denote hydrogen, halogen, cyano, nitro, trifluoromethyl, (C$_1$-C$_6$)-alkyl, (C$_1$-C$_6$)-hydroxyalkyl, (C$_1$-C$_6$)-alkoxy, (C$_1$-C$_4$)-fluoroalkoxy, —O—CF$_2$Cl—, —O—CF$_2$-CHFCl, (C$_1$-C$_6$)-alkylmercapto, (C$_1$-C$_6$)-alkylsulfinyl, (C$_1$-C$_6$)-alkylsulfonyl, (C$_1$-C$_6$)-alkylcarbonyl, (C$_1$-C$_6$)-alkoxycarbonyl, carbamoyl, N-(C$_1$-C$_4$)-alkylcarbamoyl, N,N-di(C$_1$-C$_4$)-alkylcarbamoyl, (C$_1$-C$_6$)-alkylcarbonyloxy, (C$_3$-C$_8$)-cycloalkyl, phenyl, benzyl, phenoxy, benzyloxy, anilino, N-methylanilino, phenylmercapto, phenylsulfonyl, phenylsulfinyl, sulfamoyl, N-(C$_1$-C$_4$)-alkylsulamoyl or N,N-di-(C$_1$-C$_4$)-alkylsulfamoyl, or, if A is defined as above under (a) or (c), can also together denote —(CH$_2$)$_n$— or —CH═CH—CH═CH—, with one CH$_2$ group optionally being replaced by O, S, SO or SO$_2$, R$^3$ denotes hydrogen, alkanoyl, (C$_1$-C$_6$)-alkylcarbamoyl or another physiologically tolerated protective group which can preferably be eliminated in an acid medium or under physiological conditions, R$^4$ and R$^5$ are identical or different and denote hydrogen or (C$_1$—C$_3$)-alkyl, X denotes nitrogen, and Y denotes CR$^6$, or X denotes CR$^6$, and Y denotes nitrogen, R$^6$ denotes hydrogen, halogen, (C$_1$-C$_6$)-alkyl, trifluoromethyl, (C$_1$-C$_6$)-alkoxy, —O—C$_p$H(2p+1-q)F$_q$, (C$_1$-C$_6$)-alkoxy-(C$_1$—C$_6$)-alkyl, (C$_6$-C$_{12}$)-aryl, (C$_6$-C$_{12}$)-aryl-(C$_1$-C$_6$)-alkoxy, thiophene, furan, pyrrole, imidazole, pyrazole, pyridine, tetrazole, pyrazine, pyrimidine, pyridazine, 1,2,4-triazole, thiazole, isothiazole, oxazole, isoxazole, benzothiophene, benzofuran, indole, inazole, benzimidazole, quinazoline, cinnoline, (C$_1$-C$_6$)-aryloxy, it being possible for the corresponding aryl moiety to be optionally substituted by halogen or trifluoromethyl, or denotes cyano, nitro, (C$_1$-C$_6$)-alkylamino, di-(C$_1$ -C$_6$)-alkylamino or amino, Z denotes NR$^7$R$^8$, OR$^{10}$ or SR$^{10}$, R$^7$ and R$^8$ are identical or different and denote hydrogen, (C$_1$-C$_6$)-alkyl, C$_6$-C$_{12}$)-aryl, (C$_7$-C$_{13}$)-aralkyl or (C$_3$-C$_6$)-cycloalkyl, or represent, together with the nitrogen to which they are bonded, azetidino, pyrrolidino, piperidino, piperazino, morpholino or N-(C$_1$-C$_4$)-alkylpiperazino, each of which is optionally substituted by one or two identical or different (C$_1$-C$_6$)-alkyl groups, R$^9$ denotes hydrogen, halogen, (C$_1$-C$_3$)-alkyl, C$_1$-C$_4$)-alkoxy, benzyloxy or (C$_1$-C$_7$)-alkoxy-(C$_1$-C$_3$)-alkyl, R$^{10}$ denotes hydrogen, (C$_1$-C$_4$)-alkyl, (C$_7$-C$_{13}$)-aralkyl, (C$_6$-C$_{12}$)-aryl, vinyl, allyl or a substituted alkyl radical of the formula C$_p$H(2p+1-q)F$_q$, n is 3 or 4, p is 1, 2, 3 or 4, and q is 1 to (2p+1), or its physiologically tolerated salt.

2. A compound of the formula I as claimed in claim 1, in which R$^9$ denotes hydrogen, or its physiologically tolerated salt.

3. A compound of the formula I as claimed in claim 1 in which A is as defined in claim 1 under (b), or its physiologically tolerated salt.

4. A compound of the formula I as claimed in claim 1, in which T represents —SO—, or its physiologically tolerated salt.

5. A compound of the formula I as claimed in claim 1, in which R$^1$ and R$^2$ are identical or different and denote hydrogen, (C$_1$-C$_3$)-alkyl, halogen, (C$_1$-C$_4$)-alkoxy or (C$_1$-C$_4$)alkoxycarbonyl, R$^3$ is as defined in claim 1, R$^4$ and R$^5$ each denote hydrogen, and R$^6$ denotes amino, hydrogen, halogen, (C$_1$-C$_6$)-alkyl, (C$_1$-C$_6$)-alkoxy, —O—C$_p$H(2p+1-q)F$_q$,(C$_6$-C$_{12}$)-aryloxy, (C$_6$-C$_{12}$)-aryl-(C$_1$-C$_6$)-alkoxy, it being possible for the corresponding aryl moiety to be optionally substituted by halogen or trifluoromethyl, or denotes cyano, nitro, (C$_1$-C$_6$)-alkylamino, di-(C$_1$-C$_6$)-alkylamino or (C$_1$-C$_6$)-alkoxy-(C$_1$-C$_3$)-alkyl;

R$^7$ and R$^8$ are identical or different and denote hydrogen, (C$_1$-C$_6$)-alkyl, (C$_3$-C$_6$)-cycloalkyl or phenyl, or the latter represent, together with the nitrogen to which they are bonded, azetidino, pyrrolidino, piperidino, piperazino, morpholino or N-(C$_1$-C$_4$)-alkylpiperazino, and R$^9$ and R$^{10}$ are as defined in claim 1, or its physiologically tolerated salt.

6. A compound of the formula I as claimed in claim 1, in which

R$^1$ and R$^2$ are identical or different and denote hydrogen or (C$_1$-C$_3$)-alkyl, R$^3$ denotes hydrogen, R$^4$ and R$^5$ each denote hydrogen, R$^6$ denotes hydrogen, amino, (C$_1$-C$_6$)-alkoxy, trifluoroethoxy, heptafluorobutoxy, benzyloxy, fluorobenzyloxy, difluorobenzyloxy, trifluorobenzyloxy, chlorine, nitro, cyano, methyl or ethyl, R$^9$ denotes hydrogen, R$^7$ and R$^8$ are identical or different and denote hydrogen, phenyl or (C$_1$-C$_6$)-alkyl, or the latter represent, together with the nitrogen to which they are bonded, azetidino, piperidino, pyrrolidino, morpholino, piperazino or N-(C$_1$-C$_4$)-alkylpiperazino, and R$^{10}$ denotes (C$_1$-C$_4$)-alkyl, phenyl or benzyl, or its physiologically tolerated salt.

7. A method of treating gastrointestinal disorders as well as diseases which derive from an increase in gastric acid secretion, which comprises administration of an effective amount of a compound of the formula I as claimed in claim 1, or a physiologically tolerated salt thereof.

8. A pharmaceutical formulation for treating gastrointestinal disorders as well as diseases which derive from an increase in gastric acid secretion, containing an effective amount of a compound of the formula I as claimed in claim 1, or a physiologically tolerated salt thereof, and a pharmaceutically acceptable vehicle.

* * * * *